(12) United States Patent
Burbank et al.

(10) Patent No.: US 7,377,902 B2
(45) Date of Patent: May 27, 2008

(54) BIOPSY ANCHOR DEVICE WITH CUTTER

(75) Inventors: Fred Burbank, Laguna Niguel, CA (US); Richard L. Quick, Mission Viejo, CA (US); Martin V. Shabaz, Lake Forest, CA (US); Paul Lubock, Laguna Niguel, CA (US); Michael L. Jones, Capistrano Beach, CA (US)

(73) Assignee: Senorx, Inc., Aliso Viejo, CA (US)

( * ) Notice: Subject to any disclaimer, the term of this patent is extended or adjusted under 35 U.S.C. 154(b) by 814 days.

(21) Appl. No.: 10/056,453

(22) Filed: Jan. 23, 2002

(65) Prior Publication Data
US 2003/0144605 A1 Jul. 31, 2003

Related U.S. Application Data

(63) Continuation of application No. 09/753,529, filed on Dec. 28, 2000, now Pat. No. 6,540,695, which is a continuation-in-part of application No. 09/477,255, filed on Jan. 4, 2000, now Pat. No. 6,471,700, which is a continuation-in-part of application No. 09/238,965, filed on Jan. 27, 1999, now Pat. No. 6,659,105, which is a continuation-in-part of application No. 09/356,187, filed on Jul. 16, 1999, now Pat. No. 6,312,429, which is a continuation-in-part of application No. 09/057,303, filed on Apr. 8, 1998, now Pat. No. 6,331,166, which is a continuation-in-part of application No. 09/146,185, filed on Sep. 1, 1998, now Pat. No. 6,540,693, which is a continuation-in-part of application No. 09/159,467, filed on Sep. 23, 1998, now Pat. No. 6,261,241.

(51) Int. Cl.
*A61B 10/00* (2006.01)
*A61B 18/18* (2006.01)
*A61B 17/32* (2006.01)
*A61B 17/14* (2006.01)

(52) U.S. Cl. .............. 600/564; 600/562; 600/567; 600/568; 600/570; 606/45; 606/167; 606/170; 606/171; 606/176; 606/180

(58) Field of Classification Search ............... 600/562, 600/564, 567, 568, 570; 606/45, 167, 180, 606/176, 171, 170
See application file for complete search history.

(56) References Cited

U.S. PATENT DOCUMENTS 2,032,860 A 3/1936 Wappler et al.
LISTCONT

FOREIGN PATENT DOCUMENTS

| EP | 0 970 658 | 1/2001 |
|---|---|---|
| WO | WO 02/22023 | 3/2002 |
| WO | WO 2005/063126 | 7/2005 |

OTHER PUBLICATIONS

International Search Report for PCT/US2005/027071 mailed Mar. 21, 2006.

*Primary Examiner*—Max F. Hindenburg
*Assistant Examiner*—Jeffrey G Hoekstra
(74) *Attorney, Agent, or Firm*—Edward J. Lynch

(57) ABSTRACT

A device for accessing and for isolating a desired site within a patient's body, and for obtaining a body of tissue from a patient at the site that includes an electrosurgical cutting electrode near the distal tip of a shaft, an anchoring mechanism and an electrosurgical side-cutting device. Methods are provided for accessing a target site within a patient's body, anchoring a body of tissue at the site, and isolating the body of tissue at the site. The method may be performed for a surgical biopsy or lumpectomy at the target site within a patient's body.

27 Claims, 21 Drawing Sheets

U.S. PATENT DOCUMENTS

| | | |
|---|---|---|
| 2,192,270 A | 3/1940 | McGowan |
| 3,341,417 A | 9/1967 | Sinaiko |
| 3,805,791 A | 4/1974 | Seuberth et al. |
| 3,818,894 A | 6/1974 | Wichterle et al. |
| 3,823,212 A | 7/1974 | Chvapil |
| 3,844,272 A | 10/1974 | Banko |
| 3,945,375 A | 3/1976 | Banko et al. |
| 3,955,578 A | 5/1976 | Chamness et al. |
| 4,007,732 A | 2/1977 | Kvavle et al. |
| 4,172,449 A | 10/1979 | LeRoy et al. |
| 4,197,846 A | 4/1980 | Bucalo |
| 4,202,338 A | 5/1980 | Bitroff |
| 4,243,048 A | 1/1981 | Griffin |
| 4,276,885 A | 7/1981 | Tickner et al. |
| 4,294,241 A | 10/1981 | Miyata |
| 4,294,254 A | 10/1981 | Chamness |
| 4,311,143 A | 1/1982 | Komiya |
| 4,331,654 A | 5/1982 | Morris |
| 4,362,160 A | 12/1982 | Hiltebrandt |
| 4,425,908 A | 1/1984 | Simon |
| 4,503,855 A | 3/1985 | Maslanka |
| 4,545,367 A | 10/1985 | Tucci |
| 4,565,200 A | 1/1986 | Cosman |
| 4,576,162 A | 3/1986 | McCorkle |
| 4,592,356 A | 6/1986 | Gutierrez |
| 4,616,656 A | 10/1986 | Nicholson et al. |
| 4,638,802 A | 1/1987 | Okada |
| 4,647,480 A | 3/1987 | Ahmed |
| 4,682,606 A | 7/1987 | DeCaprio |
| 4,693,237 A | 9/1987 | Hoffman et al. |
| 4,718,419 A | 1/1988 | Okada |
| 4,724,836 A | 2/1988 | Okada |
| 4,774,948 A | 10/1988 | Markham |
| 4,813,062 A | 3/1989 | Gilpatrick |
| 4,847,049 A | 7/1989 | Yamamoto |
| 4,863,470 A | 9/1989 | Carter |
| 4,909,250 A | 3/1990 | Smith |
| 4,966,583 A | 10/1990 | Debbas |
| 5,007,908 A | 4/1991 | Rydell |
| 5,024,617 A | 6/1991 | Karpiel |
| 5,035,696 A | 7/1991 | Rydell |
| 5,037,379 A | 8/1991 | Clayman et al. |
| 5,047,027 A | 9/1991 | Rydell |
| 5,059,197 A | 10/1991 | Urie et al. |
| 5,064,424 A | 11/1991 | Bitrolf |
| 5,066,295 A | 11/1991 | Kozak et al. |
| 5,078,716 A | 1/1992 | Doll |
| 5,080,660 A | 1/1992 | Buelna |
| 5,085,659 A | 2/1992 | Rydell |
| 5,100,423 A | 3/1992 | Fearnot |
| RE33,925 E | 5/1992 | Bales et al. |
| 5,111,828 A | 5/1992 | Kornberg et al. |
| 5,133,359 A | 7/1992 | Kedem |
| RE34,056 E | 9/1992 | Lindgren et al. |
| 5,147,307 A | 9/1992 | Gluck |
| 5,158,084 A | 10/1992 | Ghiatas |
| 5,158,561 A | 10/1992 | Rydell et al. |
| 5,163,938 A | 11/1992 | Kambara et al. |
| 5,192,270 A | 3/1993 | Carswell, Jr. |
| 5,196,007 A | 3/1993 | Ellman et al. |
| 5,201,732 A | 4/1993 | Parins et al. |
| 5,201,741 A | 4/1993 | Dulebohn |
| 5,207,686 A | 5/1993 | Dolgin |
| 5,215,521 A | 6/1993 | Cochran et al. |
| 5,217,458 A | 6/1993 | Parins |
| 5,221,269 A | 6/1993 | Miller et al. |
| 5,224,488 A | 7/1993 | Neuffer |
| 5,234,426 A | 8/1993 | Rank et al. |
| 5,236,410 A | 8/1993 | Granov et al. |
| 5,281,218 A | 1/1994 | Imran |
| 5,281,408 A | 1/1994 | Unger |
| 5,282,781 A | 2/1994 | Liprie |
| 5,295,990 A | 3/1994 | Levin |
| 5,304,176 A | 4/1994 | Phillips |
| 5,312,400 A | 5/1994 | Bales et al. |
| 5,318,564 A | 6/1994 | Eggers |
| 5,323,768 A | 6/1994 | Saito et al. |
| 5,324,288 A | 6/1994 | Billings et al. |
| 5,334,381 A | 8/1994 | Unger |
| 5,335,671 A | 8/1994 | Clement |
| 5,337,754 A | 8/1994 | Heaven et al. |
| 5,344,420 A | 9/1994 | Hilal et al. |
| 5,353,804 A | 10/1994 | Kornberg et al. |
| 5,368,030 A | 11/1994 | Zinreich et al. |
| 5,374,188 A | 12/1994 | Frank et al. |
| 5,376,094 A | 12/1994 | Kline |
| 5,380,321 A | 1/1995 | Yoon |
| 5,395,312 A * | 3/1995 | Desai ........................ 604/22 |
| 5,395,319 A | 3/1995 | Hirsh et al. |
| 5,397,320 A | 3/1995 | Essig et al. |
| 5,403,310 A | 4/1995 | Fisher |
| 5,409,004 A | 4/1995 | Sloan |
| 5,415,656 A | 5/1995 | Tihon et al. |
| 5,417,687 A | 5/1995 | Nardella et al. |
| 5,417,697 A | 5/1995 | Wilk et al. |
| 5,422,730 A | 6/1995 | Barlow et al. |
| 5,423,814 A | 6/1995 | Zhu et al. |
| 5,431,649 A | 7/1995 | Mulier et al. |
| 5,433,204 A | 7/1995 | Olson |
| 5,437,665 A | 8/1995 | Munro |
| 5,441,503 A | 8/1995 | Considine et al. |
| 5,449,382 A | 9/1995 | Dayton |
| 5,462,553 A | 10/1995 | Dolgin |
| 5,470,308 A | 11/1995 | Edwards et al. |
| 5,477,862 A | 12/1995 | Haga |
| 5,484,436 A | 1/1996 | Eggers et al. |
| 5,487,385 A | 1/1996 | Avitall |
| 5,488,958 A | 2/1996 | Topel et al. |
| 5,494,030 A | 2/1996 | Swartz et al. |
| 5,501,654 A | 3/1996 | Failla et al. |
| 5,507,743 A | 4/1996 | Edwards et al. |
| 5,509,916 A | 4/1996 | Taylor |
| 5,526,822 A | 6/1996 | Burbank et al. |
| 5,527,331 A * | 6/1996 | Kresch et al. ............ 606/170 |
| 5,542,948 A | 8/1996 | Weaver et al. |
| 5,549,560 A | 8/1996 | Van de Wijdeven |
| 5,554,159 A | 9/1996 | Fischer |
| 5,578,030 A | 11/1996 | Levin |
| 5,578,031 A | 11/1996 | Wilk et al. |
| 5,595,185 A | 1/1997 | Erlich et al. |
| 5,607,389 A | 3/1997 | Edwards et al. |
| 5,611,803 A | 3/1997 | Heaven et al. |
| 5,636,255 A | 6/1997 | Ellis |
| 5,643,246 A | 7/1997 | Leeb et al. |
| 5,643,282 A | 7/1997 | Kieturakis |
| 5,646,146 A | 7/1997 | Faarup et al. |
| 5,649,547 A | 7/1997 | Ritchart et al. |
| 5,653,718 A | 8/1997 | Yoon |
| 5,665,085 A | 9/1997 | Nardella |
| 5,674,184 A | 10/1997 | Hassler, Jr. |
| 5,676,925 A | 10/1997 | Klaveness et al. |
| 5,683,384 A * | 11/1997 | Gough et al. ................ 606/41 |
| 5,687,739 A | 11/1997 | McPherson et al. |
| 5,688,490 A | 11/1997 | Tournier et al. |
| 5,700,273 A | 12/1997 | Buelna et al. |
| 5,715,825 A | 2/1998 | Crowley |
| 5,720,763 A | 2/1998 | Tovey |
| 5,730,726 A | 3/1998 | Klingenstein |
| 5,735,847 A | 4/1998 | Gough et al. |
| 5,741,225 A | 4/1998 | Lax et al. |
| 5,743,906 A | 4/1998 | Parins et al. |
| 5,749,626 A | 5/1998 | Kieturakis |
| 5,749,887 A | 5/1998 | Heske et al. |
| 5,752,972 A | 5/1998 | Hoogeboom |

| | | | | | | |
|---|---|---|---|---|---|---|
| 5,755,697 A | 5/1998 | Jones et al. | | 5,913,857 A | 6/1999 | Ritchart et al. |
| 5,766,163 A | 6/1998 | Mueller et al. | | 5,925,044 A | 7/1999 | Hofmann et al. |
| 5,769,086 A | 6/1998 | Richart et al. | | 5,928,164 A | 7/1999 | Burbank et al. |
| 5,769,794 A | 6/1998 | Conlan et al. | | 5,947,964 A | 9/1999 | Eggers et al. |
| 5,772,660 A | 6/1998 | Young et al. | | 5,954,670 A | 9/1999 | Baker |
| 5,775,333 A | 7/1998 | Burbank et al. | | 5,964,716 A | 10/1999 | Gregoire et al. |
| 5,782,764 A | 7/1998 | Werne | | 5,972,002 A | 10/1999 | Bark et al. |
| 5,782,775 A | 7/1998 | Milliman et al. | | 5,980,469 A | 11/1999 | Burbank et al. |
| 5,788,709 A | 8/1998 | Riek et al. | | 5,984,919 A | 11/1999 | Hilal et al. |
| 5,794,626 A | 8/1998 | Kieturakis | | 6,004,269 A | 12/1999 | Crowley et al. |
| 5,795,308 A * | 8/1998 | Russin ................. 600/567 | | 6,022,362 A | 2/2000 | Lee et al. |
| 5,797,907 A | 8/1998 | Clement | | 6,032,673 A | 3/2000 | Savage et al. |
| 5,800,378 A | 9/1998 | Edwards et al. | | 6,056,700 A | 5/2000 | Burney et al. |
| 5,800,445 A | 9/1998 | Ratcliff et al. | | 6,063,082 A | 5/2000 | DeVore et al. |
| 5,810,764 A | 9/1998 | Eggers et al. | | 6,161,034 A | 12/2000 | Burbank et al. |
| 5,810,806 A | 9/1998 | Ritchart et al. | | 6,234,177 B1 | 5/2001 | Barsch |
| 5,814,044 A | 9/1998 | Hooven | | 6,280,450 B1 | 8/2001 | McGuckin, Jr. |
| 5,827,268 A | 10/1998 | Laufer | | 6,454,727 B1 | 9/2002 | Burbank et al. |
| 5,848,978 A | 12/1998 | Cecchi | | 6,494,881 B1 | 12/2002 | Bales et al. |
| 5,853,366 A | 12/1998 | Dowlatshahi | | 6,514,248 B1 | 2/2003 | Eggers et al. |
| 5,855,576 A | 1/1999 | Le Veen et al. | | 6,540,695 B1 | 4/2003 | Burbank et al. |
| 5,857,981 A | 1/1999 | Bucalo et al. | | 6,689,145 B2 | 2/2004 | Lee et al. |
| 5,857,982 A | 1/1999 | Milliman et al. | | 6,712,775 B2 | 3/2004 | Burbank et al. |
| 5,868,740 A | 2/1999 | LeVeen et al. | | 2003/0004407 A1 | 1/2003 | Carroll et al. |
| 5,876,340 A | 3/1999 | Tu et al. | | | | |
| 5,902,272 A | 5/1999 | Eggers et al. | | * cited by examiner | | |

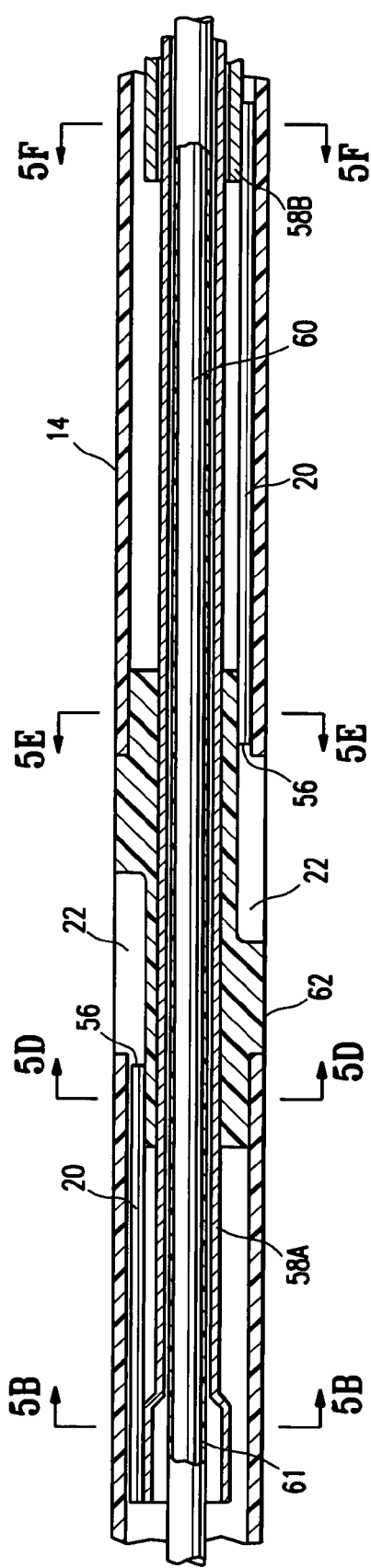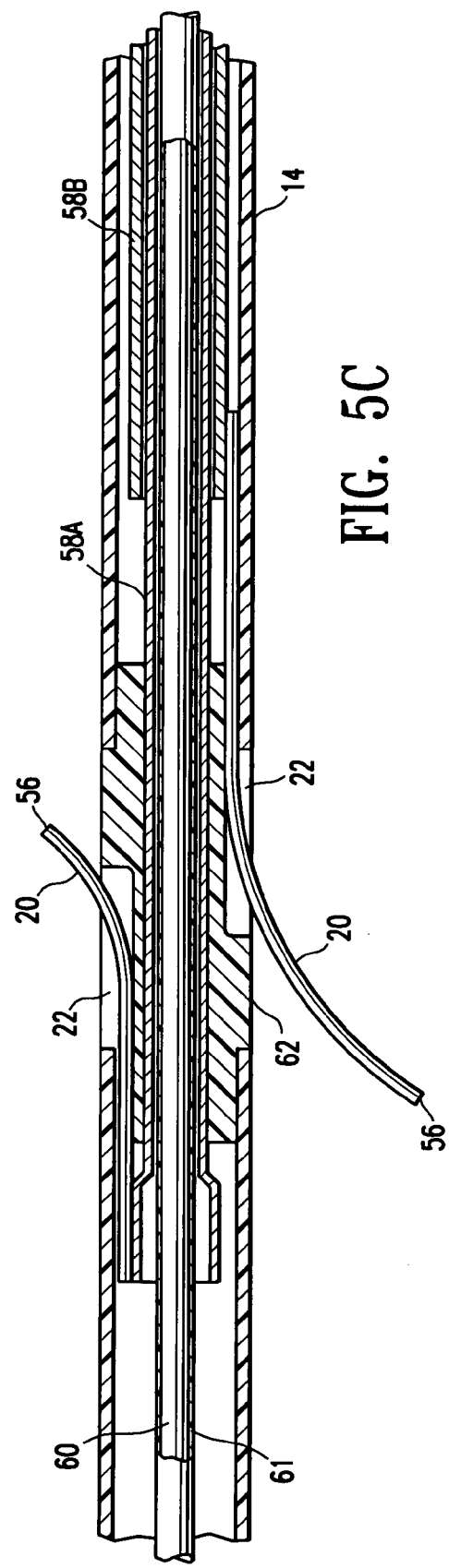
FIG. 5A
FIG. 5C

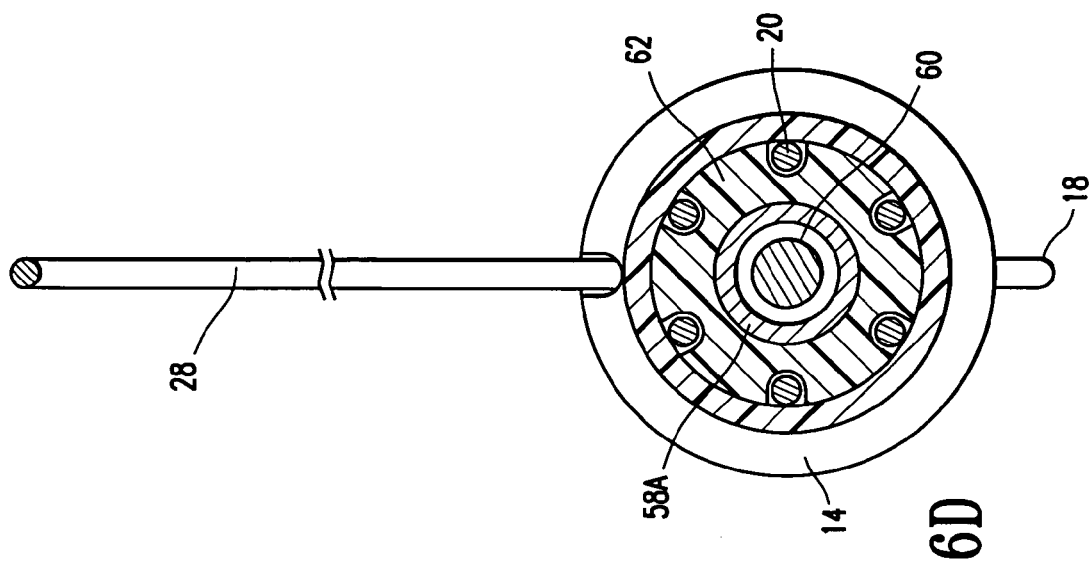
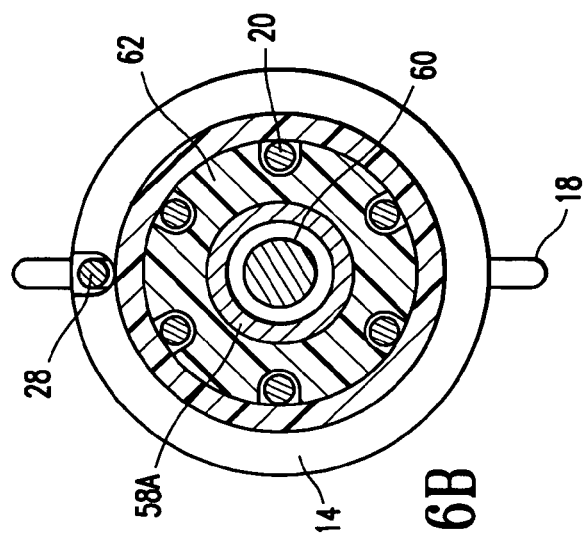

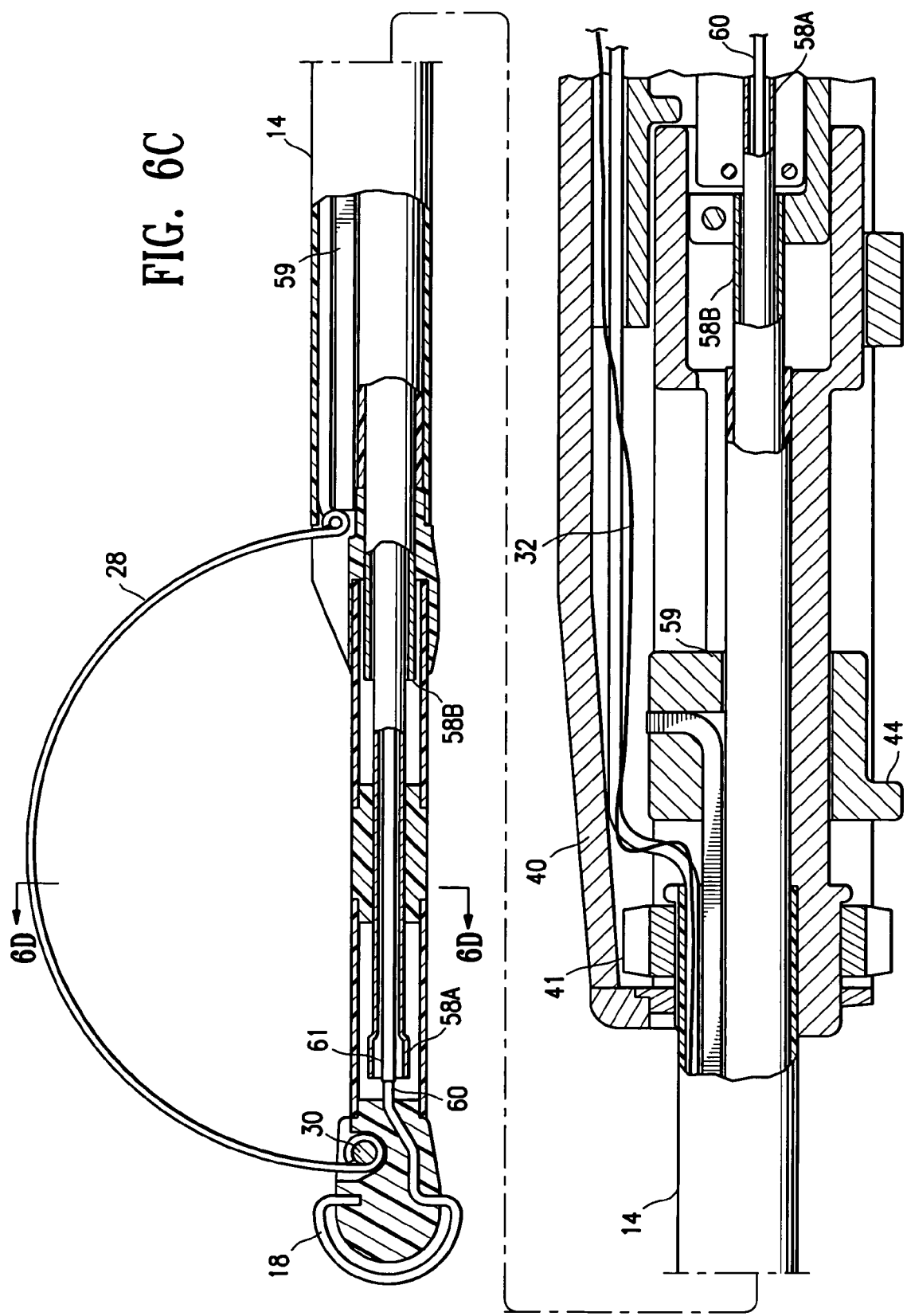

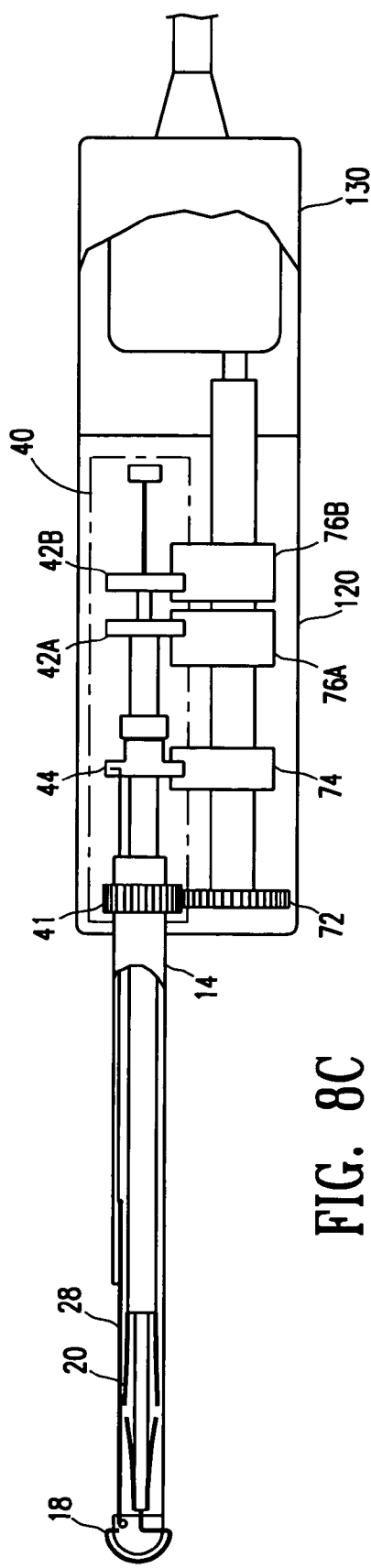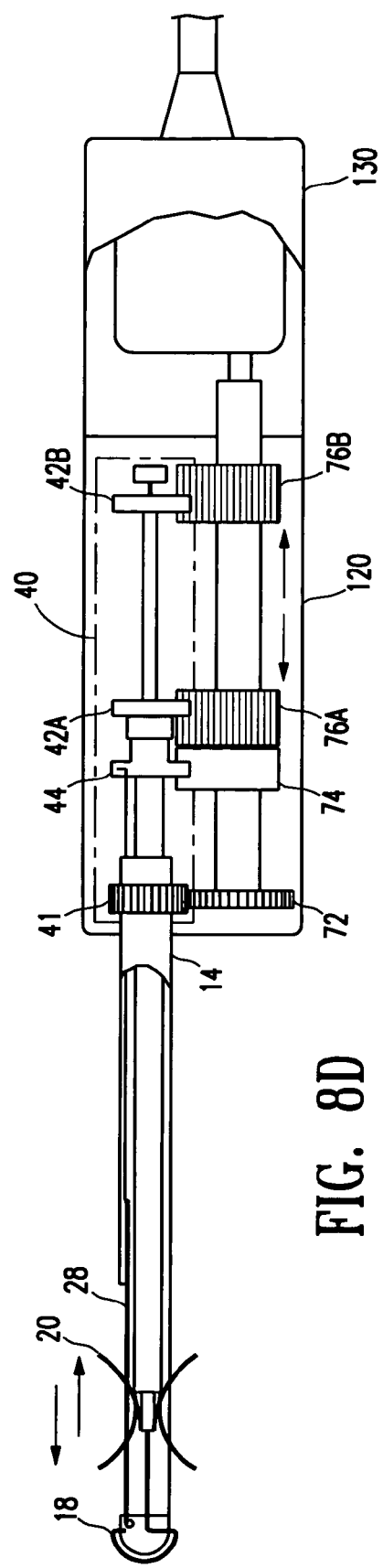
FIG. 8C
FIG. 8D

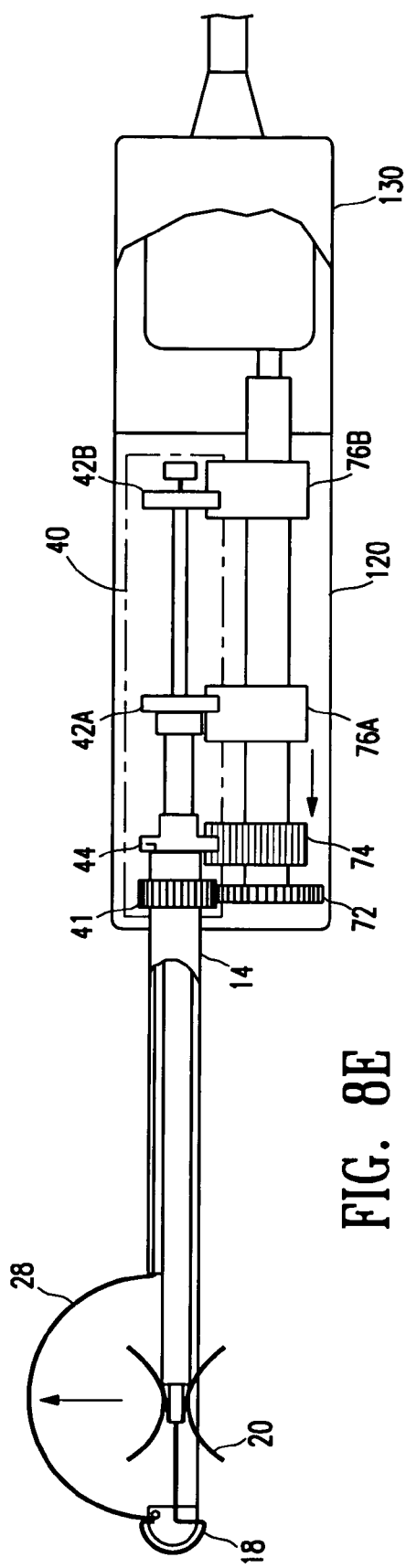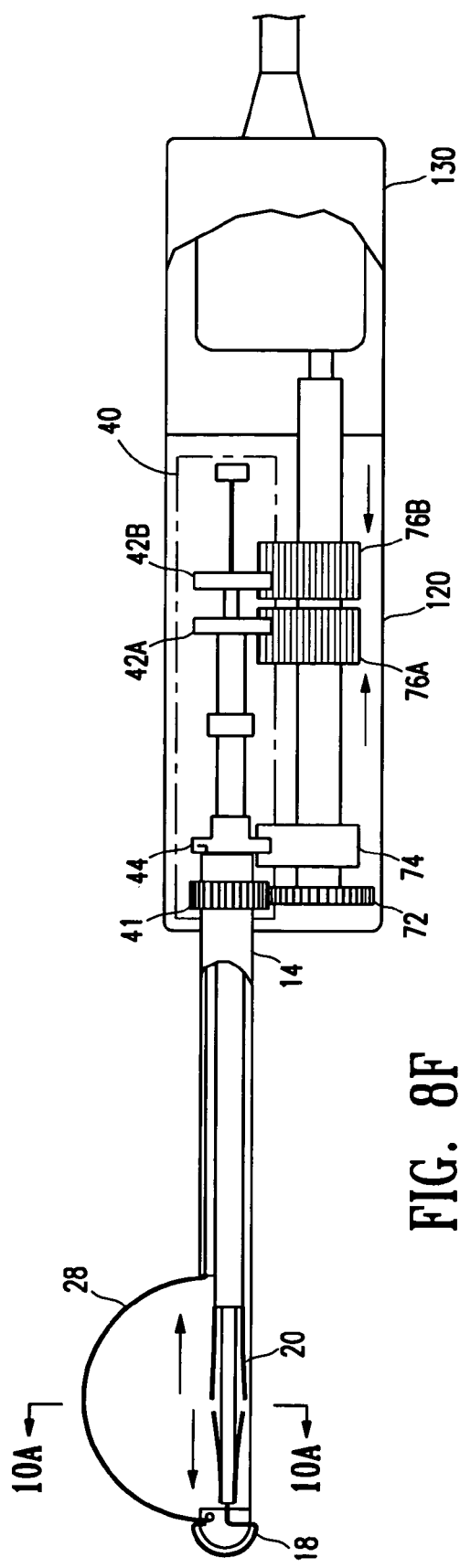

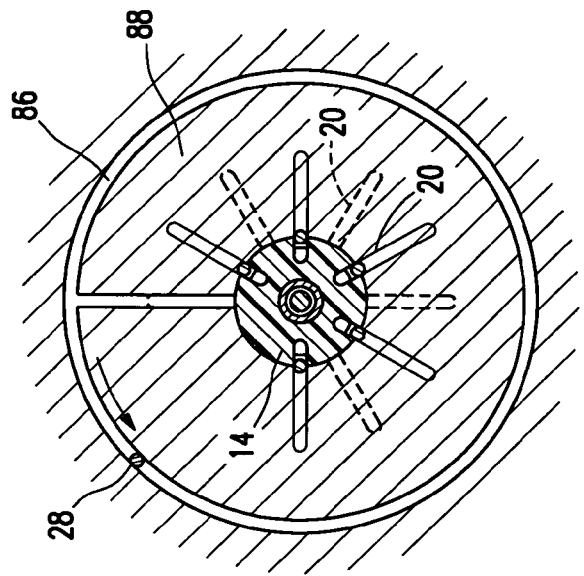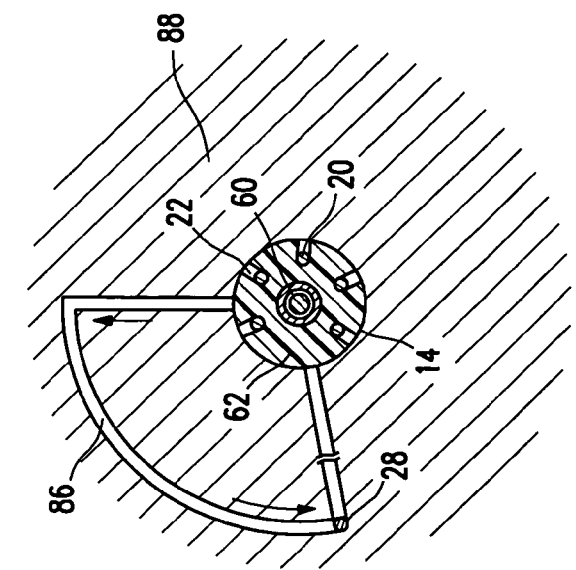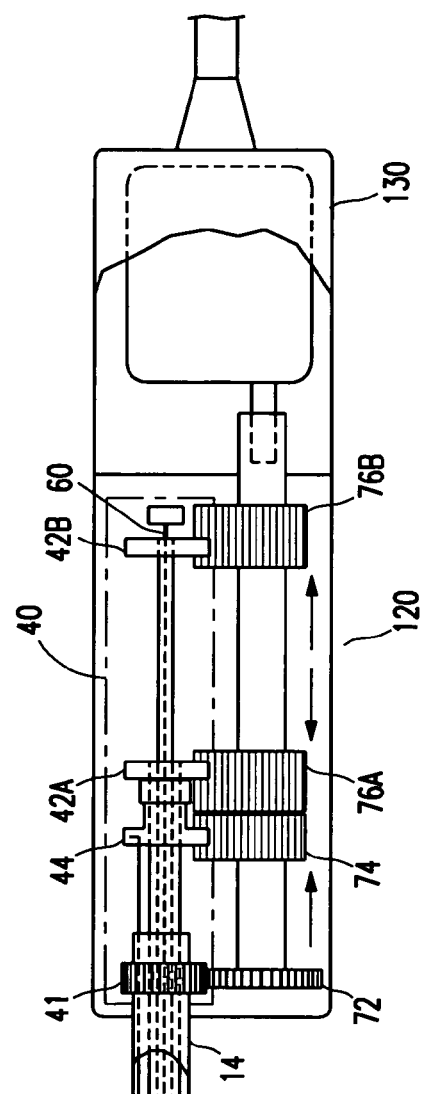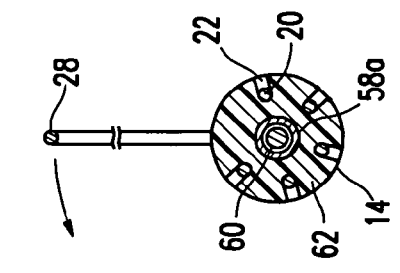
FIG. 10A
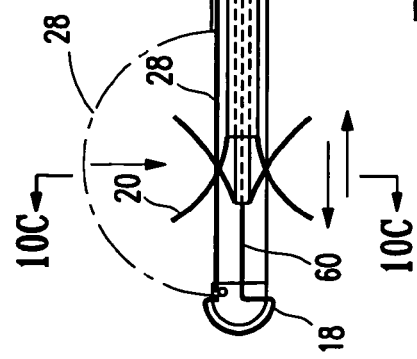

BIOPSY ANCHOR DEVICE WITH CUTTER

CROSS-REFERENCE TO RELATED APPLICATIONS

The present invention is a continuation of U.S. patent application Ser. No. 09/753,529 for "Biopsy Anchor Device with Cutter," filed on Dec. 28, 2000 now U.S. Pat. No. 6,540,695, and a continuation-in-part of U.S. patent applications Ser. No. 09/057,303 for "Breast Biopsy System and Method," filed on Apr. 8, 1998, now U.S. Pat. No. 6,331,166; Ser. No. 09/146,185 for "Methods and Apparatus for Securing Medical Instruments to Desired Locations in a Patient's Body," filed on Sep. 1, 1998 now U.S. Pat. No. 6,540,693; Ser. No. 09/159,467 for "Electrosurgical Biopsy Device and Method," filed on Sep. 23, 1998, now U.S. Pat. No. 6,261,241; Ser. No. 09/238,965 for "Tissue Specimen Destruction Device and Method Thereof," filed on Jan. 27, 1999 now U.S. Pat. No. 6,659,105; Ser. No. 09/356,187 for "Electrosurgical Lesion Location Device," filed on Jul. 16, 1999, now U.S. Pat. No. 6,312,429; and Ser. No. 09/477,255 for "Apparatus and Method for Accessing a Biopsy Site," filed on Jan. 4, 2000 now U.S. Pat. No. 6,471,700, all assigned to the assignee of the subject application, which are each hereby incorporated by reference in their entirety, and from each of which priority is claimed under 35 U.S.C. 120.

FIELD OF THE INVENTION

The present invention relates generally to the field of surgical biopsy instruments and methods. More specifically, it relates to devices and methods for electrosurgically accessing a pathologically suspect tissue mass within a patient's body, anchoring the device relative to the suspect tissue, and cutting tissue so as to isolate the suspect tissue and to facilitate the taking of a biopsy sample of the tissue mass, as well as to facilitate subsequent surgical procedures in the region of the tissue mass.

BACKGROUND OF THE INVENTION

In diagnosing and treating certain medical conditions, such as potentially cancerous tumors, it may be desirable to perform a biopsy, in which a specimen of the suspicious tissue is removed for pathological examination and analysis. In many instances, the suspicious tissue is located at a subcutaneous site, such as inside a human breast. To minimize surgical intrusion into a patient's body, it is desirable to be able to insert a small instrument into the body to gain access to the desired location for inspection and for extraction of a biopsy specimen.

Body tissue is often deformable, so that insertion of a needle or other device into a patient's tissues will often deform or displace the tissue through which the needle or other device moves. Tissues of interest, such as nodules, masses, tumors and the like, which are typically the desired targets of a biopsy sample, may be readily displaced, pushed aside or otherwise deformed during biopsy procedures, making it likely that some or all of the desired target tissue may be missed during the biopsy procedure, thereby increasing the likelihood of misdiagnosis of the condition that led to the need for the biopsy.

In extraction of a biopsy specimen with a probe, it may be desirable to anchor the probe in a desired position so as to insure that the probe remains in a proper position relative to the suspect tissue during manipulations and activities before and during the actual acquisition of the biopsy sample. In addition, it may be desirable to isolate tissue from neighboring healthy tissue in order to ensure that no diseased or abnormal tissue remains outside the sampled volume. Thus, the volume of tissue isolated may be larger than the minimum necessary so as to obtain margins of tissue free of disease for pathological diagnosis.

Electrosurgical techniques have been used in a variety of circumstances, including certain types of biopsy procedures. In electrosurgery, high frequency electrical energy is applied through a primary electrode to patient tissue. The electrical energy flows through the tissue to a return electrode that is in contact with the patent's tissue. Typically, the return electrode is attached to the patient at a point remote from where the primary electrode contacts the tissue. The tissue adjacent the primary electrode is ablated, to form an opening in the tissue.

When electrically activated, the electrode ablates the tissue adjacent the electrode, to produce a tissue opening which provides access to tissue to be taken in a biopsy sample. Guidance of the electrode tip to the desired site within a patient's body may be through stereotactic, radiological, ultrasonic, magnetic resonance imaging (MRI), or other means. However, there is frequently a delay between the positioning of the device and the taking of the biopsy sample, so that the device or tissue may move and prevent acquisition of the desired tissue. Accordingly, there is need in the art for means to mark a target site within a patient's body and for means to anchor the biopsy device in a proper location.

The tissue to be sampled or removed from the patient will often comprise a volume larger than the volume of the biopsy probe to obtain disease-free margins for pathological diagnosis. Accordingly, means for obtaining tissue samples larger than the probe itself are desired. In addition, it is of clinical interest to determine the extent of a diseased or abnormal portion of the tissue, and it is often desired that a border of normal tissue, surrounding any abnormal tissue present, be removed as well. It is further desired that the tissue to be removed be isolated from the body to prevent migration of diseased or abnormal tissue into other locations of the patient's body.

Accordingly, there is need in the art for devices and methods for accessing a desired site within a patient's body without displacing target body tissue, for anchoring devices at a desired site to prevent movement of such devices after arrival at a desired site, for isolating tissue, and for taking biopsy specimens from a patient.

SUMMARY OF THE INVENTION

The present invention is directed to systems, devices and methods for accessing target tissue within a patient, for isolating a body of target tissue from its supporting bed, for performing a lumpectomy, for performing a biopsy, and for obtaining biopsy tissue. Accordingly, the present invention provides systems, devices and methods providing access to a desired subcutaneous site for target tissue within a patient's body and for isolating such target tissue from a supporting tissue bed.

In one embodiment, a device having features of the invention has an elongated shaft having a distal end, a proximal end and a longitudinal axis. An electrosurgical electrode is secured to the distal end of the shaft with a first electrical conductor extending within the shaft having a distal end electrically connected to the electrosurgical electrode and a proximal end configured to be electrically connected to a high frequency electrical power source. An anchoring mechanism is located proximal to the distal end; and a side-cutting mechanism having a cutting element configured to be rotated about the longitudinal axis of the shaft and thereby isolate a body of target tissue.

In another embodiment, the invention is a biopsy device for obtaining target tissue within a patient. In such an embodiment, it has an elongated shaft that has distal and proximal ends and a longitudinal axis; with an electrosurgical electrode secured to the distal end of the shaft. A device of this embodiment also has an electrical conductor extending within the shaft that is electrically connected at opposite ends to the electrosurgical electrode and to an electrical power source. The device also has an anchoring mechanism and a side-cutting mechanism having a cutting element. The cutting element is configured to be rotated about the longitudinal axis of the shaft and so to isolate a body of target tissue.

In yet a further embodiment, the invention is a device for performing a lumpectomy in a patient's breast. It has an elongated shaft with an electrosurgical electrode secured to the distal end of the shaft and an electrical conductor extending within the shaft that is electrically connected to the electrosurgical electrode and to an electrical power source. The device of this embodiment has an anchoring mechanism located and a side-tufting mechanism having a cutting element that can be rotated about the longitudinal axis of the shaft to isolate a body of target tissue for removal.

In another embodiment, the invention provides a method for accessing target tissue at a desired site within a patient and isolating a body of target tissue. This method includes the steps of providing a device of the invention, contacting a patient's body with the device, and supplying high frequency electrical current to the electrosurgical electrode while advancing the device into the patient and through the site of target tissue. The method also includes steps of an anchoring mechanism to penetrate the surface of the target tissue in order to fix the device at the target tissue site. In addition, the method provides for expanding the cutting element of the side-cutting mechanism into the target tissue and rotating the cutting element to cut a body of target tissue.

In a further embodiment, the invention provides methods for performing a biopsy on target tissue at a desired site within a patient, and of performing a lumpectomy on a breast of a patient. The methods include providing a device of the invention, positioning the electrosurgical electrode of the device in contact with the patient's body, supplying high frequency electrical current to the electrosurgical electrode while advancing at least a portion of the shaft through the site of target tissue, expanding an anchoring mechanism to fix the device at the target tissue site, expanding the cutting element of the side-cutting mechanism, rotating the cutting element to form a body of target tissue, and withdrawing the device with the body of target tissue from the patient.

In one embodiment, the device of the invention has an elongated shaft with an electrosurgical electrode effective to cut through tissue and to provide access to target tissue within a patient's body. The electrosurgical electrode is configured to be electrically connected to an electrical power source. An anchoring mechanism is provided to engage the target tissue and thereby anchor the device with respect to such target tissue A side-cutting mechanism is configured to cut a body of target tissue so as to isolate the target tissue from its supporting bed.

In one presently preferred embodiment the side-cutting mechanism includes an elongated electrode oriented along the elongated shaft with one end distal to the anchoring mechanism and one end proximal to the anchoring mechanism. In this fashion the elongated electrode can isolate the target tissue. An electrical conductor extends within the elongated shaft of the device to connect to the elongated electrode of the side-cutting mechanism to an electrical power source. Preferably, a single electrical power source powers both the electrosurgical electrode and the elongated electrode of the side-cutting mechanism although the current frequency and power requirements may be different for the two electrodes.

The anchoring mechanism is an elongated member or preferably a plurality of elongated members such as wires or ribbons which can be advanced generally radially away from the elongated shaft into the body of target tissue to fix the location of the device with respect to the target tissue. The elongated members should be curved outwardly to engage the surface of the target tissue. To facilitate entry of the elongated members into the body of target tissue, in a preferred embodiment the tips are sharp. In other embodiments, the elongated members may be formed of electrically conductive material and high frequency electrical current may be applied to the elongated members. Facilitating entry of the elongated members into tissue eliminates the tenting effects which may occur when the tip of an elongated member contacts the surface of the target tissue and applies pressure thereto. The elongated members of the anchoring mechanism preferably should be movably mounted to the elongated shaft, so that they may be in a retracted configuration when the device is advanced through the patient's tissue or when the device is rotated to cut and isolate a body of target tissue, and may be extended generally radially to an expanded configuration to engage the target tissue as desired, before cutting and isolation of a body of target tissue and after such cutting and isolation.

The electrical power source is preferably a high frequency, e.g. a radio a frequency (RF), electrical power source. The frequency of the current directed to the elongated electrode of the side-cutting mechanism may be, and is preferably greater than the frequency of the current directed to the electrosurgical electrode on the distal end of the elongated shaft and the elongated members of the anchoring mechanism. For obtaining a biopsy from soft tissue such a breast tissue the electrical energy is provided in a frequency range of about 0.1 MHz to about 10 MHz. In one presently preferred embodiment, the electrical energy is provided to the electrosurgical electrode or the anchoring mechanism, or both, in a frequency range of about 0.3 to about 1.5 MHz, preferably about 0.8 MHz. In another presently preferred embodiment, the electrical energy is provided to the elongated electrode of the side-cutting mechanism in a frequency range of about 0.5 to about 10 MHz, preferably about 2.5 to about 7.5 MHz, typically about 5 MHz.

A biopsy entails removal of diseased tissue, as in a lumpectomy. A biopsy may be performed using the device of the invention by directing high frequency electrical current to the electrosurgical electrode on the distal end of the device while pressing the electrosurgical electrode of the device into the patient's tissue. The electrosurgical electrode and the distal end of the device to which it is secured readily passes through the tissue, making a cut therethrough with little or no heat affected zone at the cut surfaces of the tissue through which the device passes. The distal end of the device may be guided through the patient's tissue by an imaging system such as an ultrasonic or x-ray imaging system until the anchoring and side-cutting mechanisms are at a desired location within the target tissue. The elongated members of the preferred anchoring mechanism are then advanced out of their contracted configuration so that the distal ends thereof penetrate into the target tissue. The passage of the distal ends of the elongated members is greatly facilitated by directing high frequency electrical current through the members. The anchoring elements of the anchoring mechanism in their expanded configuration fix the device with respect to the target tissue.

The device is now ready to cut a body of tissue from the desired location. To do this, the elongated electrode of the side-cutting mechanism, preferably an arcuate electrode, is expanded outwardly while directing high frequency electrical current through the electrode making a longitudinal radial cut through the target tissue. In a preferred embodiment, the elements of the anchoring mechanism are then retracted, that is, replaced within or along the elongated shaft so that they are no longer in their deployed configuration, after the side-cutting electrode is deployed but before the side-cutting has begun cutting the margins of the tissue to be removed. At this point, preferably with the anchoring mechanism retracted, the expanded side-cutting electrode is then rotated about the longitudinal axis of the device while high frequency current is supplied thereto to separate and isolate a body of target tissue. In a preferred embodiment, the expanded side-cutting electrode rotates completely around the longitudinal axis of the device. In a most preferred embodiment, the expanded side-cutting electrode rotates more than 360°, preferably 360° plus about an additional 45°, thus insuring that a body of target tissue is entirely isolated from its supporting bed of body tissue, and that the final position of the side-cutting electrode is not directly over the slot created in the tissue as the side-cutting electrode expands outwardly during deployment.

The resulting separated and isolated body of target tissue is substantially in the shape of a spheroid, where a spheroid is a rounded shape generated by revolving a shape around an axis. By substantially in the shape of a spheroid is meant that the shape approximates a spheroid, and so is, e.g., roughly spherical, or elliptical, but may have an irregular shape that only generally approximates a spheroid. For example, the shape of the isolated body of tissue may be roughly cylindrical or conical.

The side-cutting electrode is thus effective to cut and isolate a body of tissue. Following separation and isolation of the a body of target tissue, the elements of the anchoring mechanism may be redeployed, and the device may then be removed from the body of the patient along with the isolated body of target tissue fixed by the anchoring members. In preferred embodiments, the side-cutting electrode, without being supplied with RF power, is partly retracted to aid in anchoring the isolated body of target tissue. A specimen substantially in the shape of a spheroid, such as, e.g., a rounded, substantially spherical or elliptical specimen, containing target tissue isolated by an arcuately shaped electrode greatly simplifies the pathological examination of the specimen both at its center and margins.

For removal of diseased tissue such as breast cancer, the size of the body of target tissue to be removed is usually selected to be significantly larger than the diseased tissue to ensure than all of the diseased tissue is removed. Where an isolated body of target tissue is found to have healthy tissue surrounding more centrally-located diseased tissue, a pathologist may more easily determine whether or not it is likely that any diseased tissue remains in the patient's body.

An advantage of the present invention is that it provides a roughly spherical specimen of target tissue. A roughly spherical specimen is easily examined to detect the presence and extent of diseased tissue. If the tissue within the specimen is found to be in fact diseased, e.g. to contain a carcinoma, then the entire surface of the roughly spherical specimen should be examined to be sure that there is no diseased tissue at the specimen margins. If the margins are free of diseased tissue, then the physician can be reasonably assured that all of the diseased tissue has been removed. Alternatively, the presence of diseased tissue at the margins of the specimen suggests that additional diseased tissue may remain within the patient's body.

After removing the target tissue samples or diseased tissues, additional procedures may be performed at the biopsy site or site of diseased tissue. For example, it may be desirable to cauterize, coagulate or otherwise treat the resulting cavity to stop bleeding and reduce the risk of infection or other complications. Where tissue isolation is performed, electrosurgical coagulation may be performed before or after removing the tissue specimen from the patient. Also, it may be advantageous to mark the site for future surgical procedures should pathological tests performed on the biopsy specimen indicate surgical removal or other treatment of the suspected tissue mass from which the specimen was removed. Such marking can be performed, for example, by the apparatus and method disclosed and claimed in co-pending U.S. patent application Ser. No. 09/343,975, filed Jun. 30, 1999, entitled "Biopsy Site Marker and Process and Apparatus for Applying It," which is hereby incorporated by reference in its entirety.

The devices and methods of the invention provide the advantage of anchoring the device at a target location, avoiding movement after a site of interest has been identified within the body of a patient. A further advantage is provided by the ability of the device to cut a body of tissue from that correct location, without needing to position a separate instrument at the site. In addition, the present invention provides a roughly spherical specimen of target tissue, which by its shape is easily examined to detect the presence and extent of diseased tissue.

BRIEF DESCRIPTION OF THE DRAWINGS

FIGS. 5A and 5C are longitudinal cross-sectional views of the shaft of the wand of FIG. 1 embodying features of the invention.

FIGS. 6A and 6C are longitudinal cross-sectional views of the shaft of the wand of FIG. 1 embodying features of the invention, and FIGS. 6B and 6D are transverse cross-sectional views of the shaft of the wand illustrating features of the invention showing a side-cutting electrode in retracted (6A, 6B) and extended (6C, 6D) configurations.

FIGS. 8A-8F provide partially cut-away perspective views of a surgeon's disposable unit illustrating features of the invention.

FIG. 10 provides partially cut-away side-views of the wand of FIG. 1 embodying features of the invention and transverse cross-sectional views of the wand and breast tissue during a procedure embodying features of the methods of the invention. FIG. 10D is a partially cut-away side-view of the wand. FIGS. 10A-10C are transverse cross-sectional views of the wand, FIGS. 10B and 10C also including transverse cross-sectional views of breast tissue, during a procedure embodying features of the methods of the invention.

DETAILED DESCRIPTION OF THE INVENTION

Figure 1:
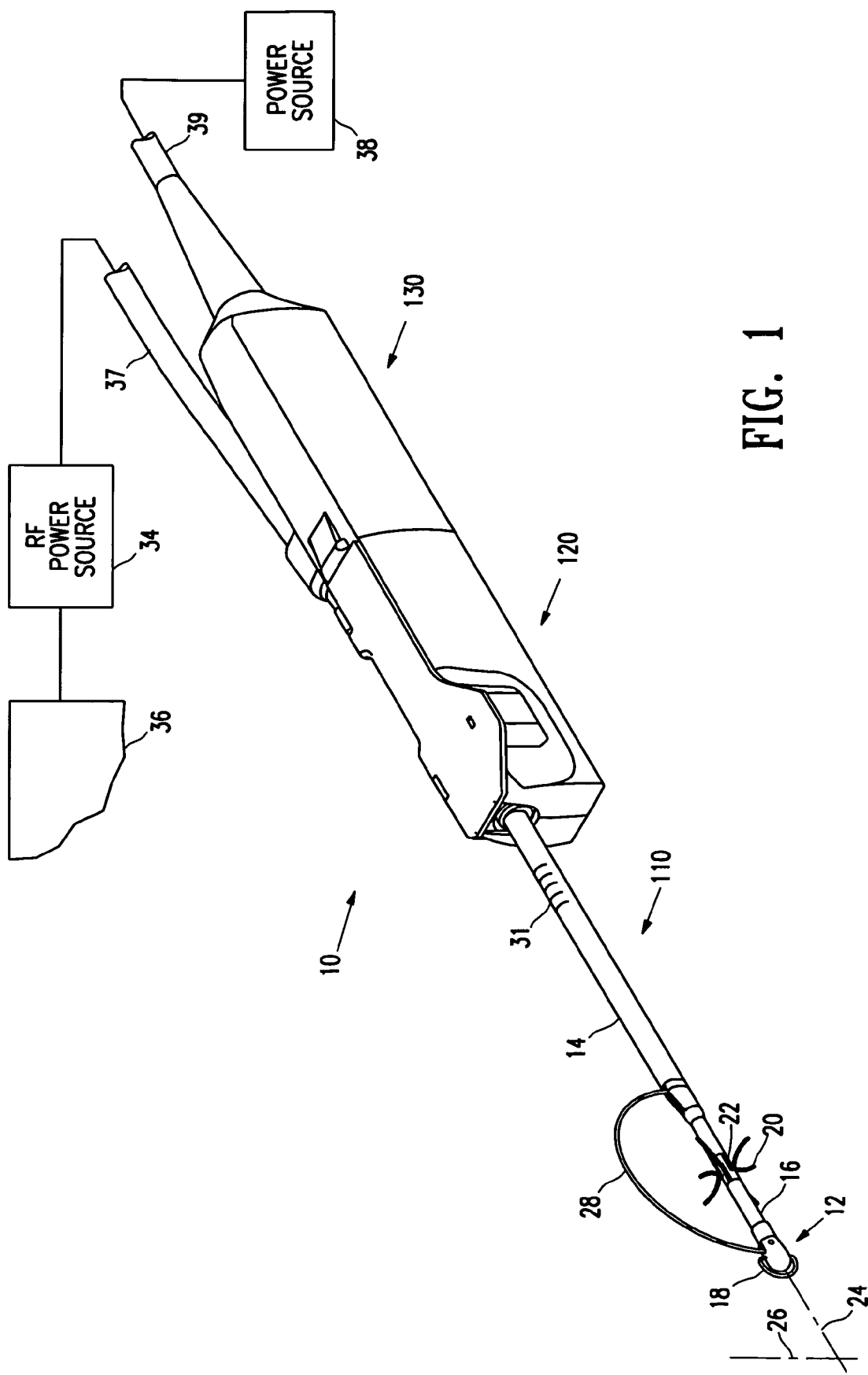
FIG. 1 is a perspective view of a tissue removing system illustrating features of the invention.

In FIG. 1 and in all succeeding figures, like elements are indicated by like numerals. Reference is made to FIG. 1, showing a system of the invention 10 comprising an electrosurgical device, or wand, 110, a surgeon's disposable unit 120, and a motor unit 130. These devices may be used to access target tissue within a patient, to isolate a body of target tissue from its supporting bed, to perform a biopsy on target tissue at a desired site within a patient, or to perform a lumpectomy on a breast of a patient. When assembled together, the devices form a system for accessing tissue within a patient's body, including, in various aspects, a biopsy system and a lumpectomy system. These systems further comprise devices for anchoring tissue that has been accessed, or for ablating tissue that has been accessed. A portion of wand 110 is illustrated in FIG. 1. The wand 110 comprises an electrosurgical device that includes a distal tip 12 situated at the distal portion 16 of a shaft 14. Situated near the distal tip 12 of the shaft 14 is an electrosurgical electrode 18. Shaft 14 has a longitudinal axis 24 that is effective to define a radial direction 26 perpendicular to longitudinal axis 24. The anchoring mechanism may be comprised of anchor elements, such as metallic wires or ribbons, extending radially (that is, extending at least in part in a radial direction 26) from shaft 14; similarly, the ablation mechanism may be comprised of ablation elements, such as metallic wires or ribbons, extending at least in part radially from shaft 14, the metallic wires or ribbons of an ablation mechanism preferably being longer than those of an anchoring mechanism. An anchoring mechanism may be capable of serving also as an ablation mechanism where it is used during rotary motion of the device or where sufficient electrical power is conducted to the metallic ribbons or wires. The radial wires 20 shown in the Figures thus illustrate either an anchoring mechanism or an ablation mechanism or both. Radial wires 20 emerge from radial wire slots 22 situated at a position proximal to the distal tip 12 along shaft 14. Although the radial wires 20 are shown in FIG. 1 deployed in their extended configurations, it will be understood that they may also retract into slots 22 in their retracted configuration, as is shown in subsequent Figures.

The devices of the invention also comprise a side-cutting mechanism. A side-cutting mechanism is illustrated in the Figures as side-cutting electrode 28, comprising an arcuate band or ribbon electrode when deployed in its extended configuration. Thus, a side-cutting mechanism of the invention is shown in FIG. 1 as side-cutting electrode 28 effective for cutting tissue and for isolating tissue in a patient. Side-cutting electrode 28 lies along shaft 14 when retracted and assumes an arcuate configuration when deployed (as, e.g., illustrated in FIG. 1). However, it will be understood that in other embodiments of the invention side-cutting electrode 28 may be provided with a slot into which it may be retracted.

Surgeon's disposable unit 120 is effective to engage and hold wand 110, and to work together with it. Both wand 110 and surgeon's disposable unit 120 are preferably sterile. In preferred embodiments, wand 110 and surgeon's disposable unit 120 are not reusable, but are instead meant to be used for one procedure only. Surgeon's disposable unit 120 is operably connected to RF power source 34 and ground plate 36 via cable assembly 37, the cable assembly 37 comprising at least one conductor effective to carry RF power. In preferred embodiments, cable 37 is connected to RF power unit 34 via a plug-in connection, so that surgeon's disposable unit 120 and RF power unit 34 may be readily connected or disconnected as desired. In most preferred embodiments, the cable is adapted to provide for efficient transfer of RF power to the wand, by impedance matching, capacitance minimization, or other means for maximizing the efficiency of RF power transfer. Electrical contact between surgeon's disposable unit 120 and wand 110 when wand 110 is seated in and held by surgeon's disposable unit 120 is effective to provide wand 110 with RF power from RF power source 34. Such RF power may be supplied to electrosurgical electrode 18, to radial wires 20 and to side-cutting electrode 28 via at least one conductor in wand 110. Effective electrical contact between ground plate 36 and the patient is provided during a clinical or surgical procedure by placement of ground plate 36 in contact with the patient. Electrical contact between ground plate 36 and a patient may be enhanced by application of conductive gels or creams to the skin of the patient, and by other methods known to those of ordinary skill in the art as well. Where the elements 18, 20 and/or 28 are operably connected to a source of RF power 34, and where a patient is in contact with a ground plate 36 operably connected to a source of RF power 34, contacting a patient with an electrosurgical electrode 18, radial wire 20, and/or side-cutting electrode 28 is effective to allow the passage of RF power between the element 18, 20 and/or 28 and the patient, effective to allow RF cutting or penetration by the elements 18, 20 and/or 28, as desired, effective to allow the element to penetrate the patient's tissues. Where the element is a radial wire 20 that is an ablation element, such passage of RF power is effective to ablate tissue in contact with the element. Where the element is an electrosurgical electrode 18, a radial wire 20 that is an anchoring element, or a side-cutting electrode 28, such passage of RF power is effective to cut the tissue, and optionally to coagulate the tissue as well. It will be understood that RF power source 34 may comprise more than one source of RF power.

It will be understood that all electrical devices require a complete electrical circuit to function. The complete circuit required for the proper functioning of an electrosurgical device may be either monopolar or bipolar; that is, the return electrical path may be to a ground electrode distant from the point of delivery of electrical power, such as RF power, or may be to a ground electrode near to or on the same instrument.

With a monopolar device, the return electrical path is provided through a ground electrode, such as ground pad 36. With a bipolar device, the return electrical path from the primary electrode (such as the electrosurgical electrode 18, radial wires 20, or the side-cutting electrode 28) is provided by a return electrode carried on the same instrument, such as wand 110. In preferred embodiments, the electrosurgical devices of the invention are monopolar electrosurgical devices.

In addition to providing operable electrical connection between wand 110 and RF power source 34, surgeon's disposable unit 120 is effective to provide or transfer mechanical force to wand 110 when wand 110 is engaged and held by surgeon's disposable unit 120.

Motor unit 130 provides mechanical force, such as rotary motion, effective to drive or rotate a shaft or shafts (e.g., co-axial shafts) operably connected to it. As illustrated in FIG. 1, motor unit 130 is operably connected to surgeons' disposable unit 120 (which may comprise a shaft able to be operably connected to motor unit 130) and receives power via power connection 39. It will be understood that motor unit 130 could contain an electric motor or motors and power connection 39 could comprise an electrical cable; alternatively, motor unit 130 may comprise one or more hydraulic or pneumatic motors, and power connection 39 could comprise a conduit for hydraulic or pneumatic fluid or gas. It will be understood that motor unit 130, power connection 39, and associated elements may be positioned and adapted in any suitable manner effective to provide motive force via motor unit 130 to surgeon's disposable unit 120. Motor unit 130 can engage and work with surgeon's disposable unit 120 effective to provide or transfer mechanical force to surgeon's disposable 120, which is itself effective to provide or transfer mechanical force to wand 110 when wand 110 is engaged and held by surgeon's disposable unit 120. Motor unit 130 is typically not a sterile device, although it may be used in sterile procedures when routine precautions known to those of ordinary skill in the art are taken. For example, motor unit 130 may be covered with a sterile cover or wrap, such as a sterile "sock," for use in a sterile procedure with wand 110 and surgeon's disposable unit 120.

Wand 110 comprises a shaft portion and a housing portion. As illustrated in FIG. 2, the shaft portion comprises shaft 14 and associated elements, such as electrosurgical electrode 18, radial wires 20, and side-cutting electrode 28, while the housing portion comprises housing 40 and associated elements. A portion or portions of shaft 14 may be contained within housing 40. Elements associated with housing 40 include those elements contained within housing 40 that are also mounted on shaft 14, such as shaft gear 41, radial wire shuttles 42A and 42B, and side-cutting electrode shuttle 44. Shaft gear 41 is operably connected to shaft 14, so that rotation of shaft gear 41 is effective to rotate shaft 14. Rotation of shaft 14 may be effected by the engagement of shaft gear 41 with a suitable drive gear. In preferred embodiments, such a drive gear is provided by drive gear 72 in surgeon's disposable unit 120, shown in FIG. 8. It will be understood by those of ordinary skill in the art that there are many suitable ways to rotate portions of the device, or to rotate the entire device, and that any suitable mechanism for effecting rotation of the device or of the elongated shaft, and in particular, rotation of side-cutting electrode around the longitudinal axis 24 of shaft 14 will be suitable for the practice of the invention.

In FIG. 2 the distal direction is shown to the left, towards electrosurgical electrode 18 located at distal tip 12, and the proximal direction is shown opposite the distal direction. Shuttles 42A, 42B, and 44 are mounted along the shaft 14 within housing 40, and are effective to move proximally and distally in longitudinal directions along portions of shaft 14 located within housing 40. Radial wire shuttles 42A and 42B are operably connected to radial wires 20, and side-cutting electrode shuffle 44 is operably connected to side-cutting electrode 28.

Figure 2A:
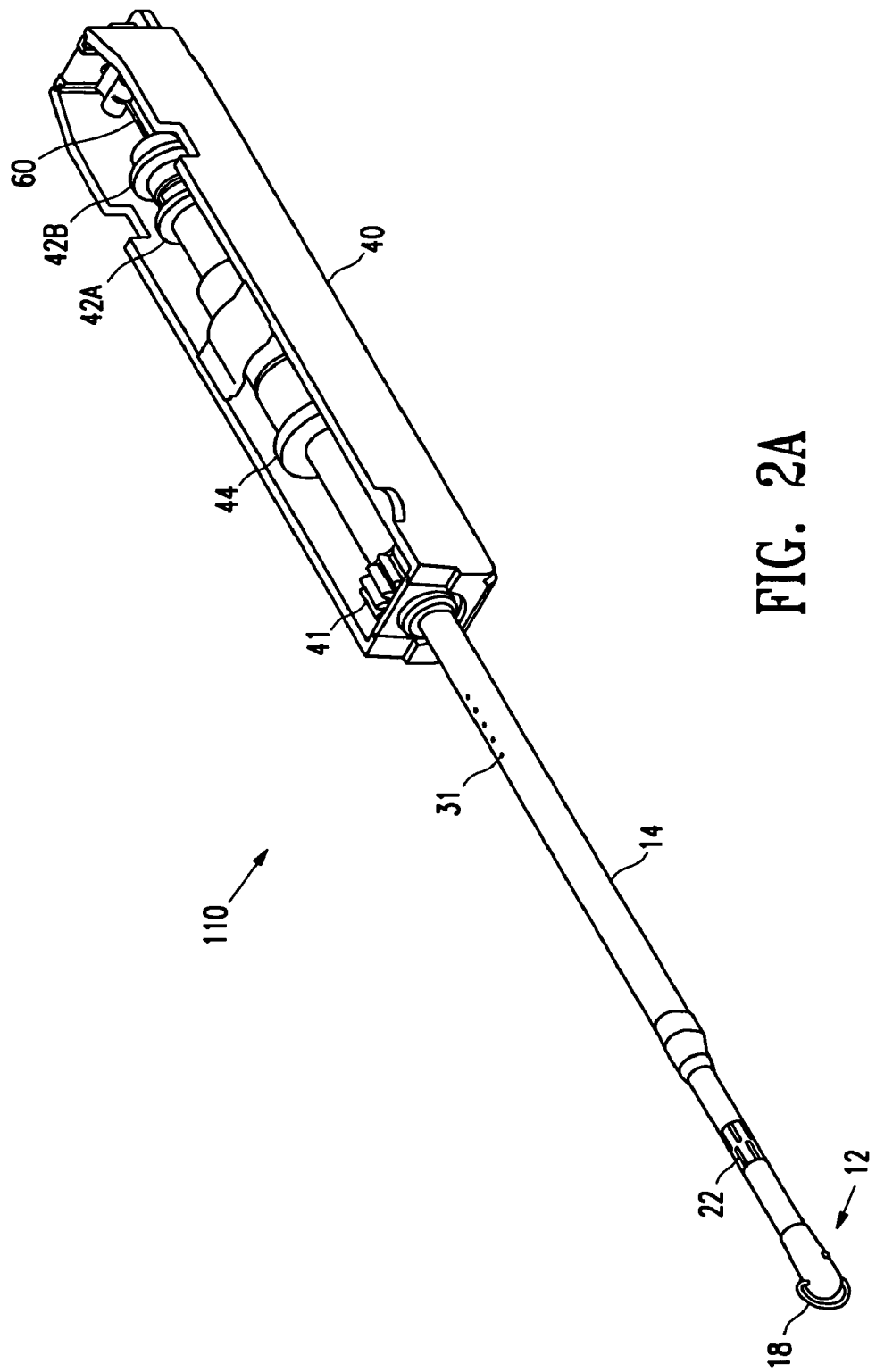
FIG. 2A is a perspective view of a device with radial wires and side-cutting wire electrode retracted.
Figure 2B:
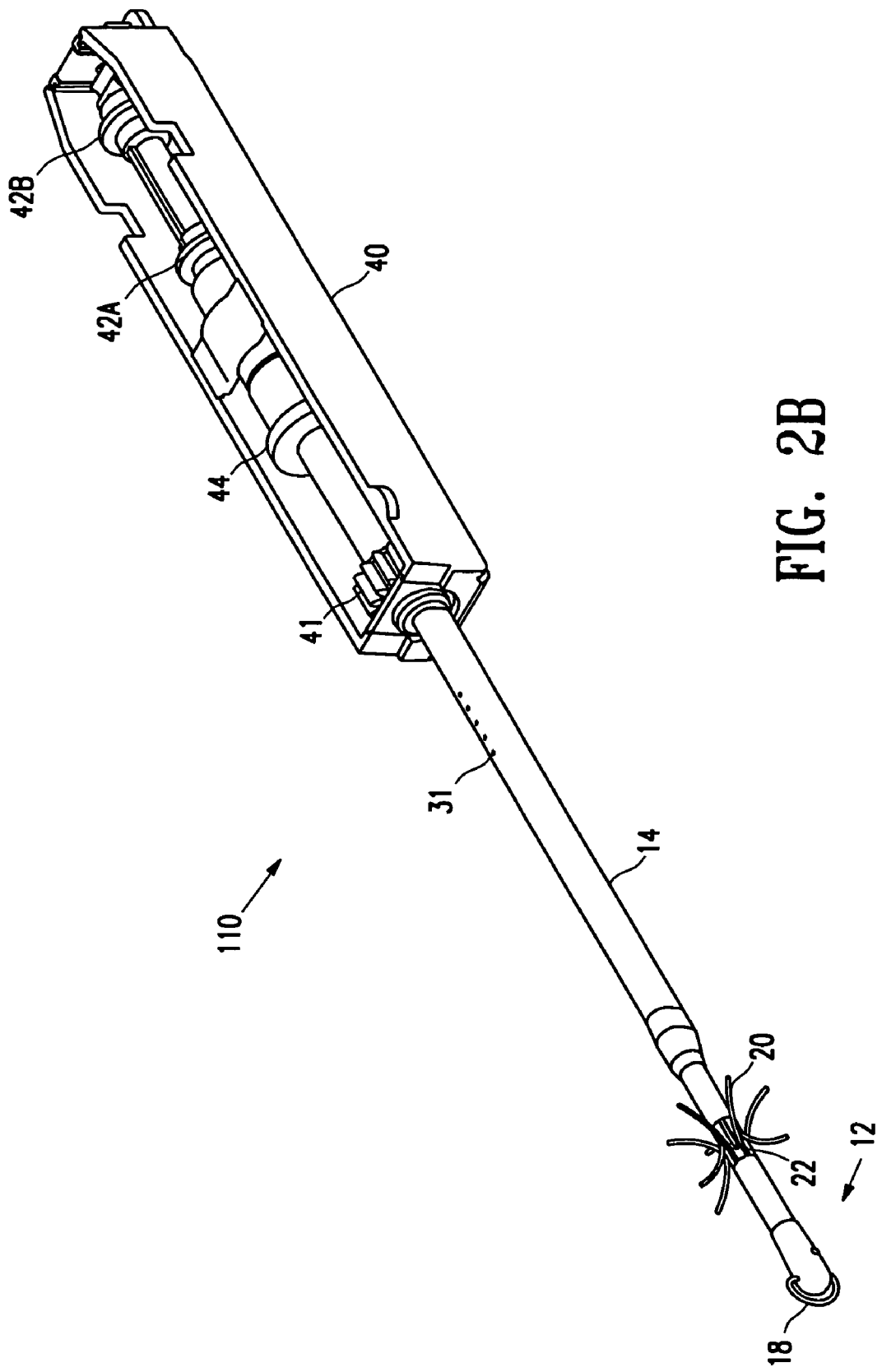
FIG. 2B a perspective view of a device with radial wires extended.
Figure 2C:
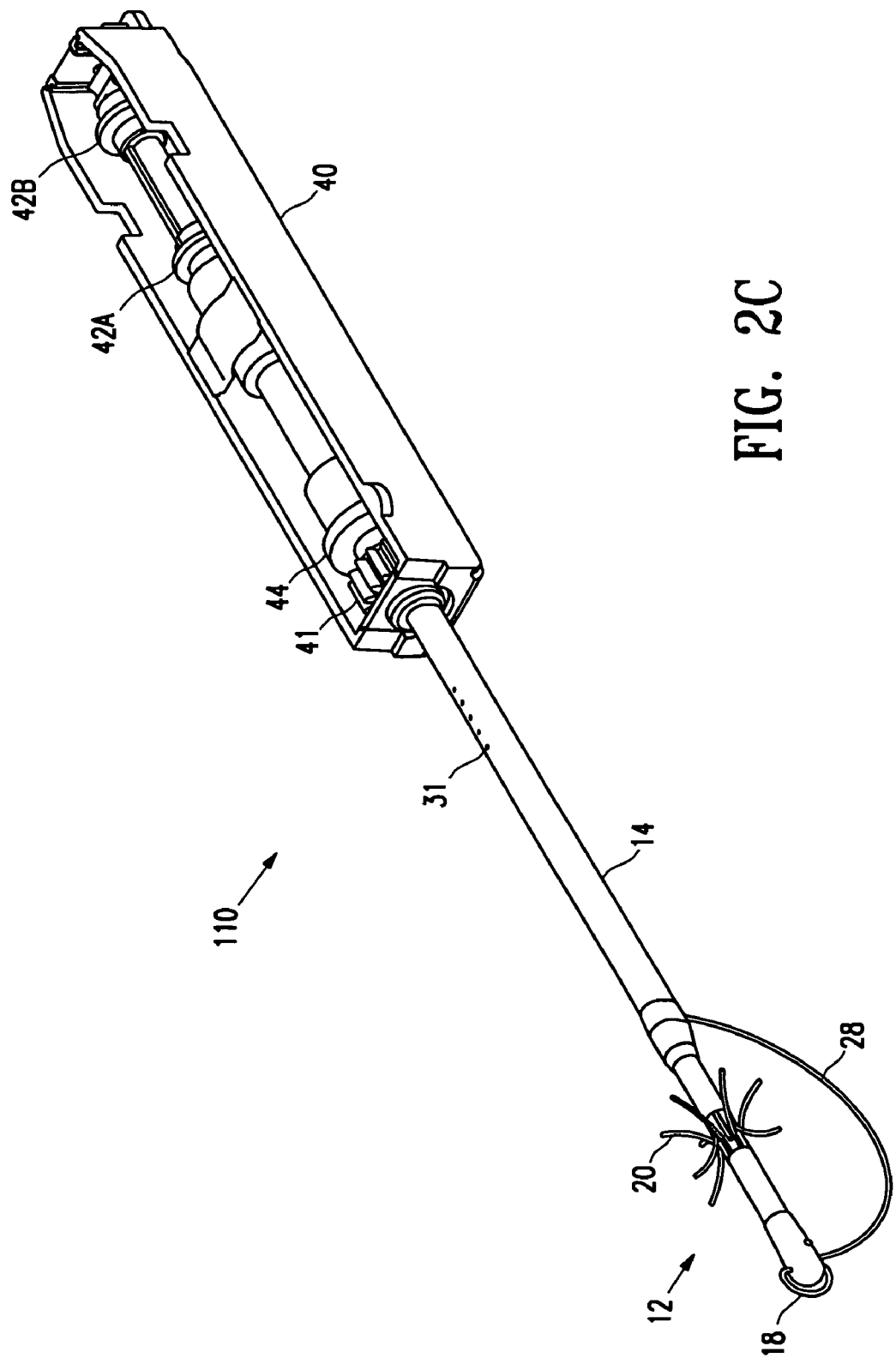
FIG. 2C a perspective view of a device with radial wires and side-cutting electrode extended.
Figure 2D:
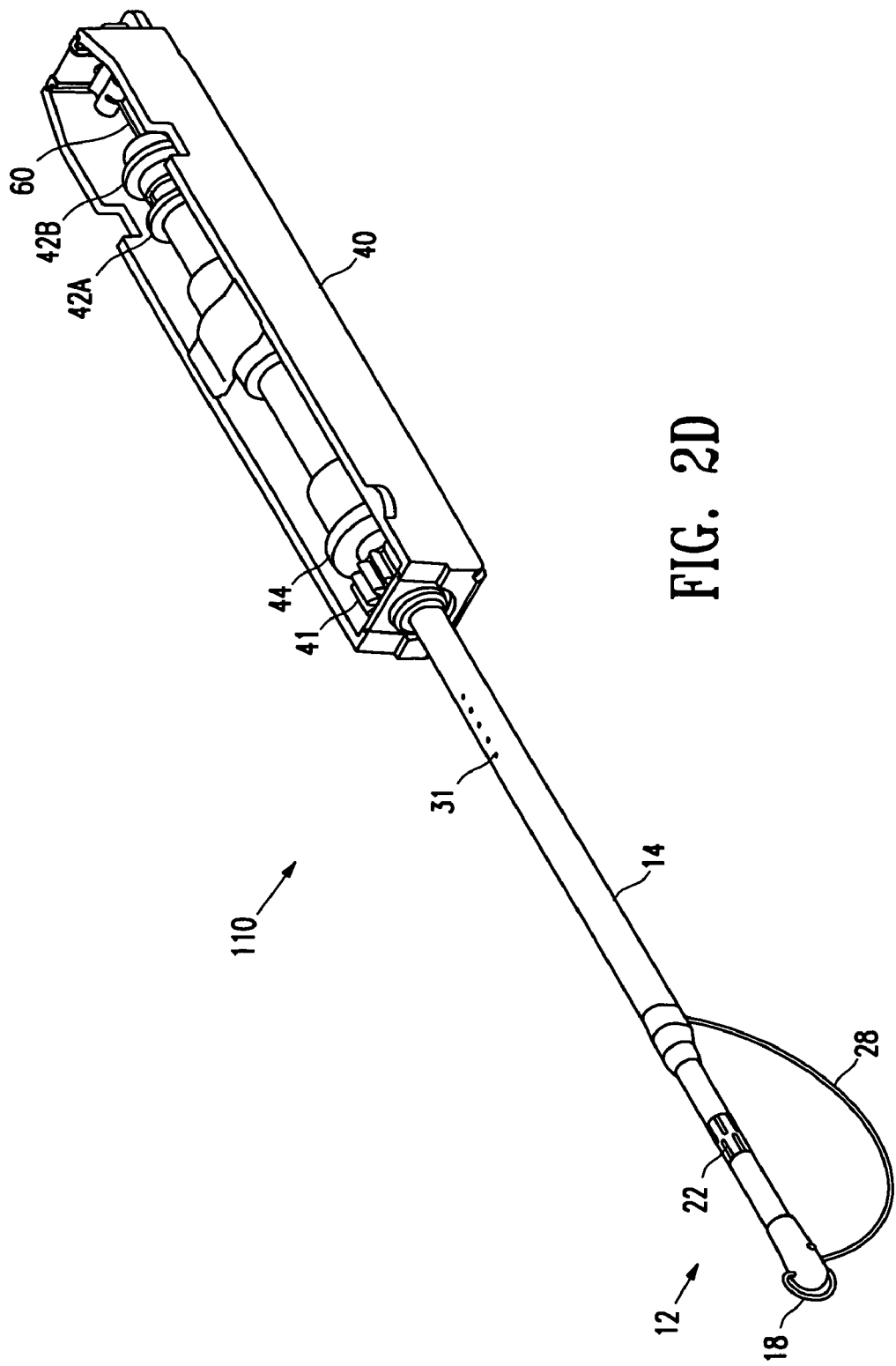
FIG. 2D a perspective view of a device with the side-cutting electrode extended.

As shown in FIGS. 2B and 2C, when radial wire shuttles 42A and 42B are separated from each other, and are located in their most proximal and distal positions, the radial wires 20 are deployed in their extended configurations. Similarly, when side-cutting electrode shuttle 44 is in its most proximal position, as shown in FIGS. 2C and 2D, the side-cutting electrode 28 is deployed in its extended configuration. As shown in FIG. 2A and 2D, when radial wire shuttles 42A and 42B are located adjacent to each other, the radial wires 20 are in their retracted configuration. Similarly, when side-cutting electrode shuttle 44 is in its most distal position, as shown in FIGS. 2A and 2B, the side-cutting electrode is in its retracted configuration.

Electrosurgical electrode 18 may be operably connected to a source of RF power, such as 34 shown in FIG. 1. In preferred embodiments, such connection is via conductors in wand 110, operably connected to conductors in handle 46 connected to a source of RF power. Such conductors may be, for example, conductor 60. In preferred embodiments, the source of RF power for electrosurgical electrode 18 is not the same source of RF power for side-cutting electrode 28. In preferred embodiments, electrosurgical electrode 18 requires lower frequency RF power than does side-cutting electrode 28. Contacting a patient with the electrosurgical electrode 18 while the patient is in contact with a ground plate 36 and electrosurgical electrode is supplied with RF power allows an operator to penetrate a patient's body with device 110 by guiding the electrosurgical electrode 18 into the patient to access tissue within a patient's body.

The wand 110 may be inserted into a patient's body to position the distal tip 12 or shaft 14 at a desired site or a targeted tissue site (e.g., a suspected lesion or tumor) in the patient, thereby providing access to the targeted tissue site. In preferred embodiments, handle 46 holds wand 110 as shaft 14 is inserted into position in a patient; in preferred embodiments, handle 46 is also used to deploy anchor wires 20. In one embodiment, shaft 14 can have a length of about 3 to about 15 cm, preferably, about 5 to about 13 cm, and more preferably, about 9 to about 11 cm.

To assist in properly locating the elongated shaft 14 during advancement of the wand 110 into a patient's body, (as described below), the shaft 14 may be optionally provided with indicators 31. The tip 12, shaft 14 and other supporting parts of device 110 may be made of any suitable material. In some embodiments, the tip, 12, elongated shaft 14 and other parts of device 110 may be made of a sturdy, high impact biocompatible material such as medical grade polymer (e.g., high density polyethylene (HDPE), polycarbonate, fluorocarbon polymers, such as fluorinated ethylene propylene (FEP) polymer, or other polymer known in the art). In preferred embodiments, shaft 14 comprises polycarbonate. In other embodiments, the shaft 14 may be comprised of biocompatible polymer tubing, such as polyethylene, polyimide, ether sulfone, polysulfone, or the like. The shaft 14 may be optionally coated with a lubricious coating such as, for example, a Teflon® (polytetrafluoroethylene) coating, or other hydrophilic coating, Shaft 14 may have, but need not have, a circular cross-section. In some embodiments, shaft 14 has an oval cross-section. Other cross-sectional shapes are also suitable, including square, rectangular, triangular, and irregular cross-sectional shapes. In addition, the cross-sectional shape and the width of shaft 14 may vary along its length. Accordingly, the width of shaft 14 may vary according to the position and method of determining such width. However, one measure of the width, or cross-sectional dimension, of shaft 14 is a radial dimension extending from one lateral surface to an opposite lateral surface of shaft 14 taken along a line perpendicular to longitudinal axis 24. In one embodiment, shaft 14 has a radial dimension of about 0.5 to about 20 mm, preferably of about 1 to about 10 mm, more preferably of about 1 to about 5 mm. However, it will be understood by those of skill in the art that suitable radial dimensions may vary, and may vary depending on the location or condition of the tissue to be sampled, so that suitable radial dimensions within the scope encompassed by the present invention include radial dimensions greater than 10 mm and radial dimensions lesser than 1 mm.

The wand 110 has a distal tip 12 from which an electrosurgical electrode 18 protrudes. The distal tip may comprise mica/glass composite, medical grade polymer as exemplified above, or other suitable material. The electrosurgical electrode 18 can be formed of conductive wire or ribbon. It will be understood that any biocompatible material, including steel, tungsten, nitinol, and other conductive biocompatible materials are suitable to form an electrosurgical electrode 18. An electrosurgical electrode 18 may comprise conductive wire or ribbon of between about 0.005 inches to about 0.030 inches in diameter, preferably between about 0.01 inches to about 0.02 inches, more preferably about 0.014 inches in diameter. In preferred embodiments, the electrosurgical electrode is made of stainless steel, such as 300 series or 17-7 stainless steel or equivalent, for example 302 stainless steel wire of approximately 0.014 in. (approximately 0.36 mm) diameter. As shown in the Figures, a portion of the electrosurgical electrode may be semi-circularly shaped, although it will be understood by one of ordinary skill in the art that a variety of shapes are suitable for the practice of the invention. The electrosurgical electrode 18 is in direct electrical contact with the RF power source 34. When the electrosurgical electrode 18 is electrically activated with high frequency electrical energy and placed in contact with tissue, electrical energy flows through the tissue to a return electrode (such as ground plate 36) that is also in contact with the patient. The tissue adjacent the electrosurgical electrode 18 is ablated to create an incision as the electrosurgical electrode 18 passes through the tissue. The electrosurgical electrode 18 can have a radius, subtending a maximum width approximately equal to or slightly greater than the maximum cross-sectional dimension of the elongated shaft 14, so that during the electrosurgical process, the electrosurgical electrode 18 makes an opening through the tissue sufficiently large to receive the elongated shaft 14. In a preferred embodiment of the invention, the maximum width of the electrosurgical electrode 18 is approximately 1.5 times the maximum outside radial dimension of the elongated shaft 14. In preferred embodiments, the maximum width of the electrosurgical electrode 18 can be from about 2 to about 14 mm, preferably, about 4 to about 12 mm, and more preferably, about 7 to about 9 mm. It will be understood by those of skill in the art that the electrosurgical electrode may be of any suitable size and shape effective to produce an incision to allow passage of the wand 110 through the patient's tissue to provide access to desired tissue within a patient and to provide for isolation of desired tissue within a patient.

Optional markings 31 along shaft 14 may be used to aid an operator in gauging the depth of penetration into a patient. In preferred embodiments, the operator is aided in the guidance of such penetration by imaging apparatus and techniques such as ultrasound, x-ray imaging, magnetic resonance imaging, computer tomography, and other methods known in the art.

The side-cutting electrode 28 may comprise an elongated electrode with a distal end, a proximal end and a middle portion. In a most preferred embodiment, a side-cutting electrode follows an arcuate path (as shown in FIGS. 1 and 2, and in subsequent figures) in a direction substantially parallel to a longitudinal axis 24 of the elongated shaft 14. In the embodiment shown, the side-cutting electrode 28 thus lies in a plane substantially parallel to a radius 26 of the elongated shaft 14. It will be understood by those of skill in the art that the shapes of side-cutting electrodes may differ from the arcuate shape illustrated in FIGS. 1 and 2. For example, suitable shapes of side-cutting electrodes include shapes with angles and straight portions as to well as smooth curves. It will be understood that the side-cutting electrode is effective to cut, ablate, coagulate and/or cauterize tissue when supplied with RF power, and the patient placed in contact with a ground plate 36, similar to that described for the electrosurgical electrode 18.

A side-cutting electrode 28 can be formed of conductive wire or ribbon, and may be made of any suitable material effective to conduct RF power to tissues. It will be understood that any biocompatible material, including steel, tungsten, nitinol, and other conductive biocompatible materials are suitable to form a side-cutting electrode 28. In preferred embodiments side-cutting electrodes comprise metals such as tungsten, tungsten alloys, and stainless steel, for example 300 series or 17-7 stainless steel or an equivalent. In most preferred embodiments, the side-cutting electrode 28 comprises tungsten. Side-cutting electrodes may be, for example, about 0.001 to about 0.04 inches in diameter, preferably between about 0.005 and about 0.02 inches in diameter, most preferably about 0.01 inches in diameter.

In FIG. 1, radial wires 20 are shown extending in radial directions from the elongated shaft 14, while radial wires 20 are retracted in FIGS. 2A and 2D. Thus, FIGS. 1 and 2 illustrate embodiments of the invention in which the radial wires 20 are mounted to shaft 14 effective to allow their deployment and retraction. In preferred embodiments, the radial wires may extend or retract from shaft 14 via radial wire slots 22 to positions of greater or lesser radial extension. Thus, in deploying, the radial wires are effective to expand outwardly from the elongated shaft of the device; when such expansion is effected after shaft 14 has been inserted into a patient's tissues, and while shaft 14 remains within a patient's tissues, the expansion of the radial wires is effective to penetrate into a patient's tissue. In preferred embodiments, penetration of radial wires 20 into a patient's tissues may be aided by sharpening the radial wire tips. Penetration of radial wires may also be aided by supplying RF power to the radial wires. In embodiments comprising an anchoring mechanism, where the radial wires 20 comprise anchoring elements and where penetration is aided by supplying RF power to the radial wires, the radial wires 20 may comprise conductive material such as a metal and may be insulated along their length except near to their tips 56, which are conductive and not insulated. In preferred embodiments comprising an ablation mechanism where the radial wires comprise ablation elements, the radial wires comprise conductive material, such as a metal, and may receive RF power.

In a contracted configuration, with the radial wires 20 withdrawn into slots 22, the radial wires present no obstacle to movement of the shaft through a patient's tissues, such as advancement through, or rotation within, body tissue. When deployed in a radially expanded configuration, with RF power not connected to the radial wires 20, radial wires 20 are effective to prevent movement of the shaft and of the device 110, and so to hold the device 110 in position. In a preferred embodiment, radial wires 20 are housed in shaft 14, are capable of emerging from shaft 14 from radial wire slots 22, and optionally deploy to variable length outside the shaft 14. It will be understood by those of skill in the art that radial wires 20 may comprise a variety of shapes and lengths, that any suitable means for attaching radial wires 20 to shaft 14, any suitable means for housing the radial wires within shaft 14, and any suitable means for extension of the radial wires into adjacent tissue effective to anchor the wand 110 at a desired site within a patient are all within the scope of the invention. Such radial wires 20 may be, for example, between about 0.003 inches to about 0.02 inches in diameter, preferably between about 0.05 inches to about 0.015 inches in diameter, more preferably about 0.009 in. (0.23 mm) in diameter. In preferred embodiments, radial wires 20 may be formed of 300 series stainless steel, 17-7 stainless steel or an equivalent. Radial wires 20 may be partially coated with an insulating coating such as a polymer with high dielectric strength, for example, polyimide, so that only part of the wire, such as a part near the tip 56, is exposed and is able to pass current into surrounding tissue. In alternative embodiments, radial wires 20 may be modified so as to comprise an optical fiber capable of providing illumination, or hollow to allow deposition of dye or marker substances, so as to facilitate visualization of the anchor elements.

The electrosurgical electrode 18, radial wires 20 and the side-cutting electrode 28 may be operably connected to an RF power source. For example, an electrical connection between side-cutting electrode 28 and a source of RF power may be comprised of Litz wire, preferably of suitable length to allow for the extension and rotation of side-cutting electrode 28. It will be understood by those of skill in the art that any suitable electrical power source may be used. In use, where at least one of the electrosurgical electrode 18 or radial wires 20 or side-cutting electrode 28 are monopolar electrodes, a portion of the patient's body will be placed in contact with the ground plate 36 to provide electrical continuity and a complete circuit. Alternatively, where the electrosurgical electrode 18 and side-cutting electrode 28 and anchor wires 20 are all bipolar electrodes, the ground plate 36 will be unnecessary for cutting, and may be omitted, with electrical continuity provided by both of the poles of the bipolar electrodes or by a return electrode located near to the electrosurgical electrode 18, side-cutting electrode 28 and anchor wires 20.

As shown in FIG. 3, wand 110 may be inserted into tissue and anchored in place using handle 46 as system 140. Wand 110 fits into notch 51 shown in FIG. 3A, and may be seated in and engaged by handle 46 so that wand 110 may be carried and is guided by an operator for use in a biopsy or surgical procedure. Handle 46 provides electrical connection between wand 110 and RF power unit 34 and ground 36 via cable assembly 37 and provides mechanical control of radial wires 20 via the radial wire shuttles 42A and 42B. FIG. 3A shows wand 110 with the radial wires 20 retracted, while FIG. 3B shows wand 110 with radial wires 20 deployed in the extended configuration. Depression of plunger assembly 47 of handle 46 is effective to deploy radial wires 20, as illustrated in FIG. 2B, while retraction of plunger assembly 47 is effective to retract radial wires 20, as illustrated in FIG. 3A. It will be appreciated that many methods of effecting the deployment and retraction of radial wires 20 are suitable for the practice of the invention, and all such are within the scope of the invention.

Figure 3A:
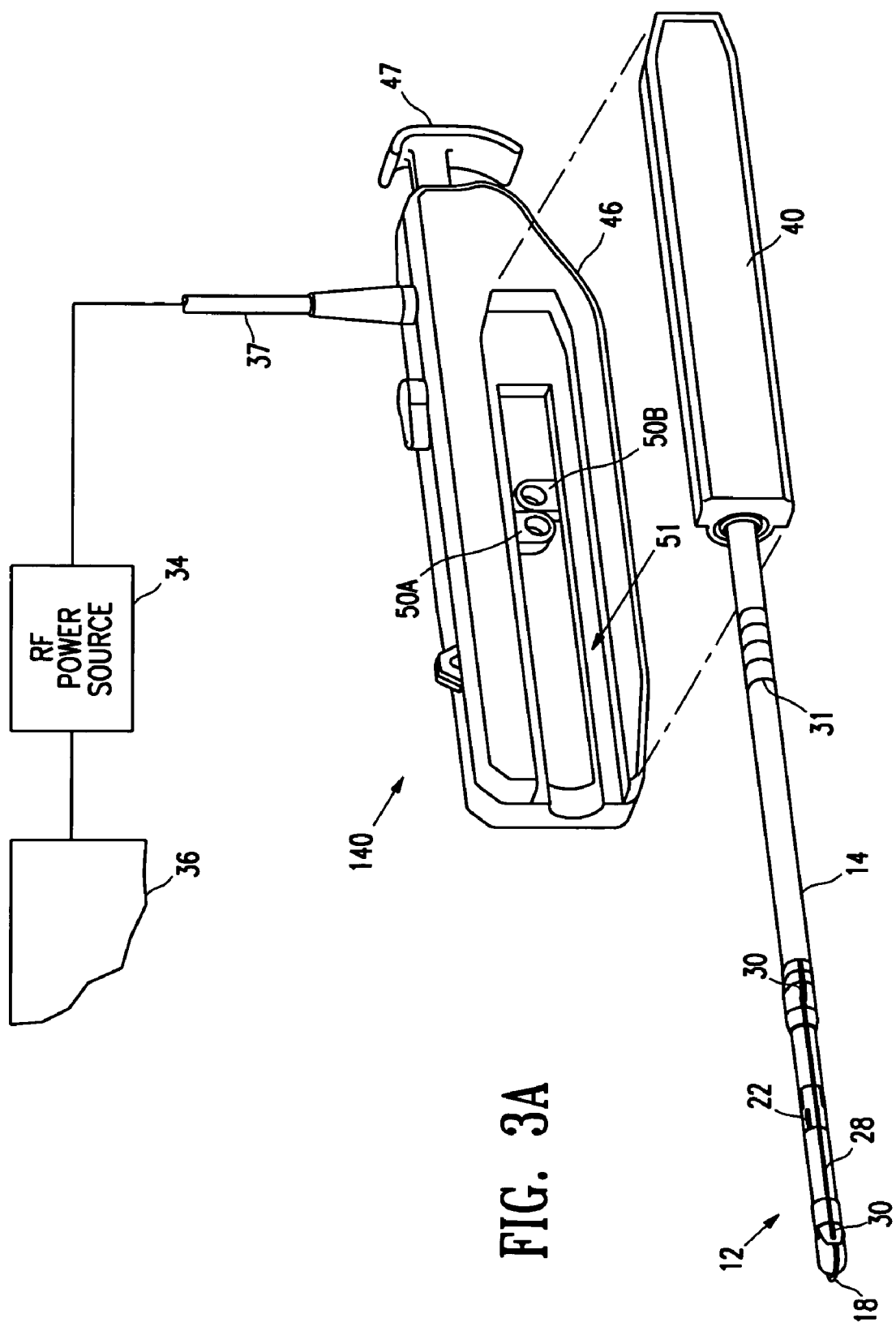
FIG. 3A a perspective view of a wand with radial wires and side-cutting electrode retracted.
Figure 3B:
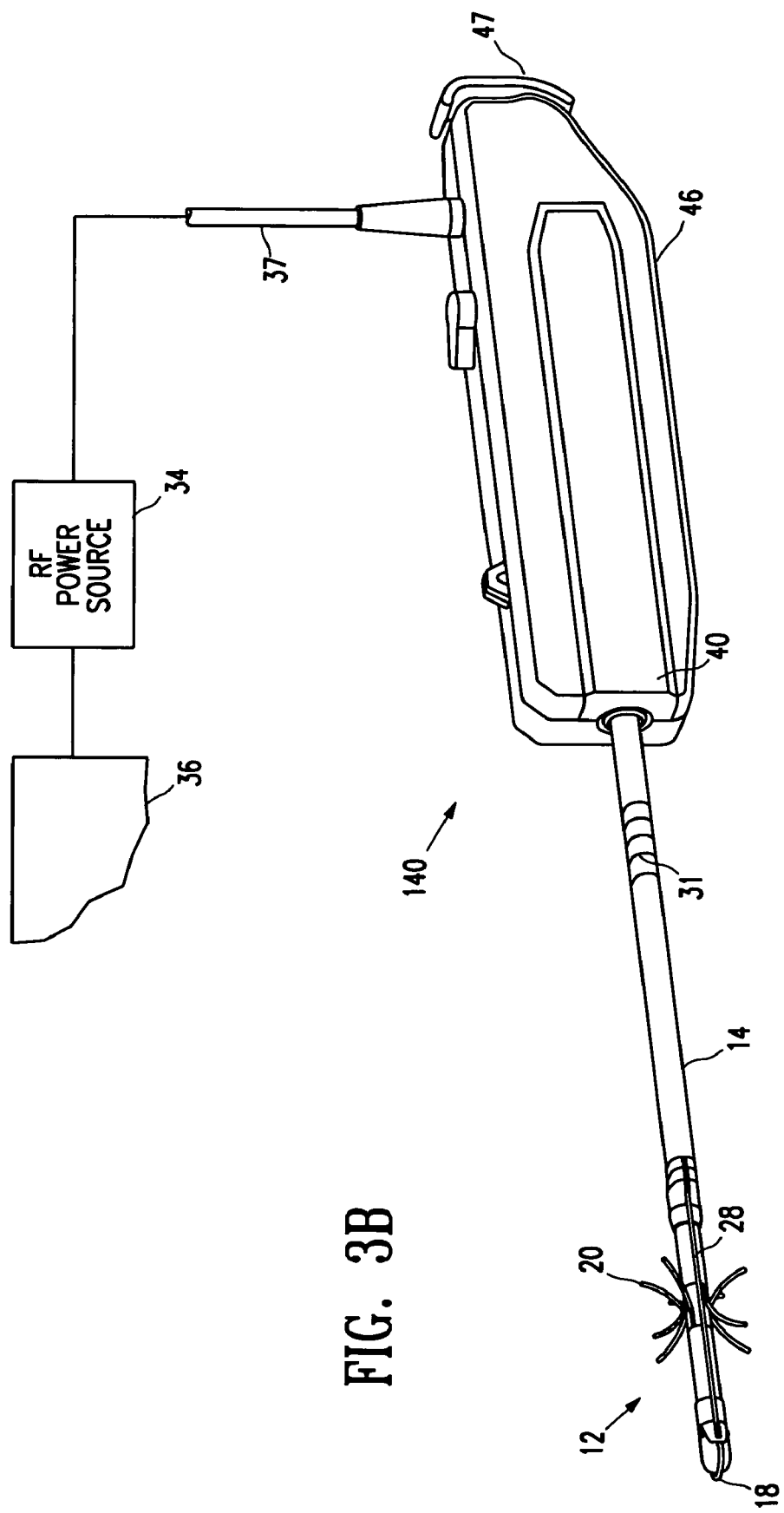
FIG. 3B a perspective view of a wand with radial wires and side-cutting electrode extended.
Figure 3C:
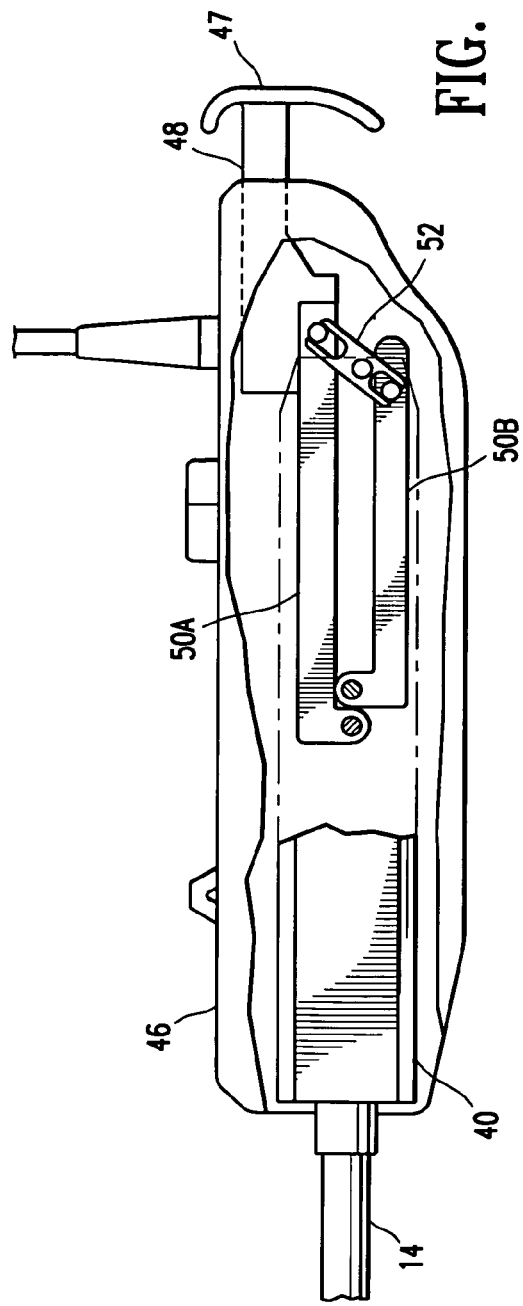
FIG. 3C is a partially cut-away view of a handle embodying features of the invention, showing a plunger mechanism embodying features of the invention with a plunger extended.
Figure 3D:
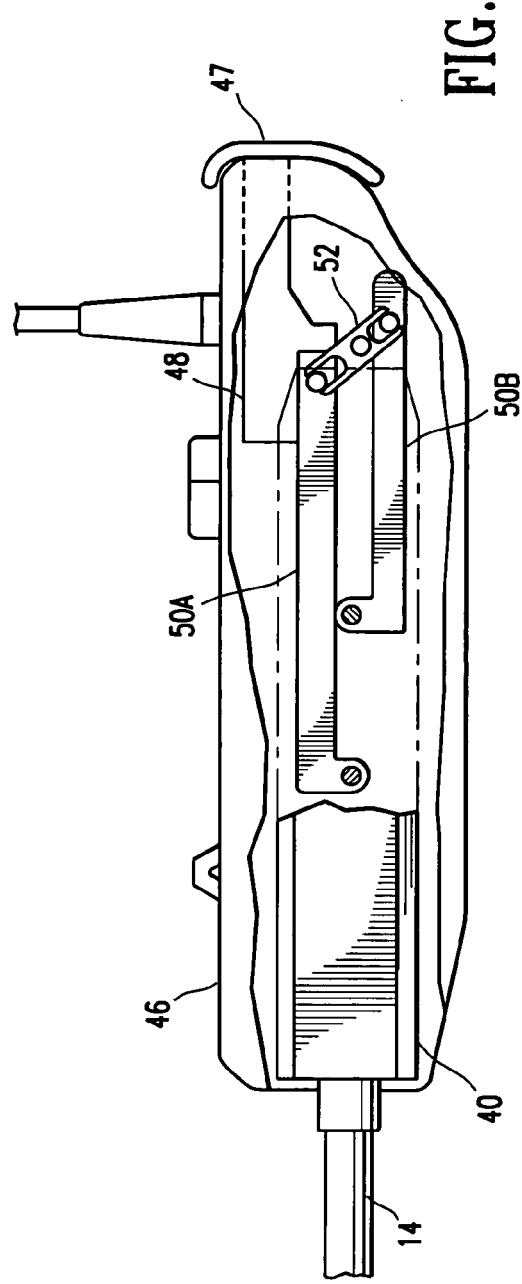
FIG. 3D is a partially cut-away view of a handle embodying features of the invention, showing a plunger mechanism embodying features of the invention with a plunger depressed.

A preferred embodiment of handle 46 is illustrated in partially cut-away views in FIGS. 3C and 3D, showing manual shuttle clasps 50A and 50B and pivot assembly 52. Manual shuttle clasps 50A and 50B are effective to engage radial wire shuttles 42A and 42B when wand 110 is seated in notch 51 of handle 46. Plunger 47 connects with plunger shaft 48 to provide an operable connection to shuttle clasp 50A, shown in FIGS. 3C and 3D, so that depression or retraction of plunger assembly 47 moves shuttle clasp 50A effective to move pivot assembly 52 causing opposite motion of shuttle clasp 50B.

Figure 4B:
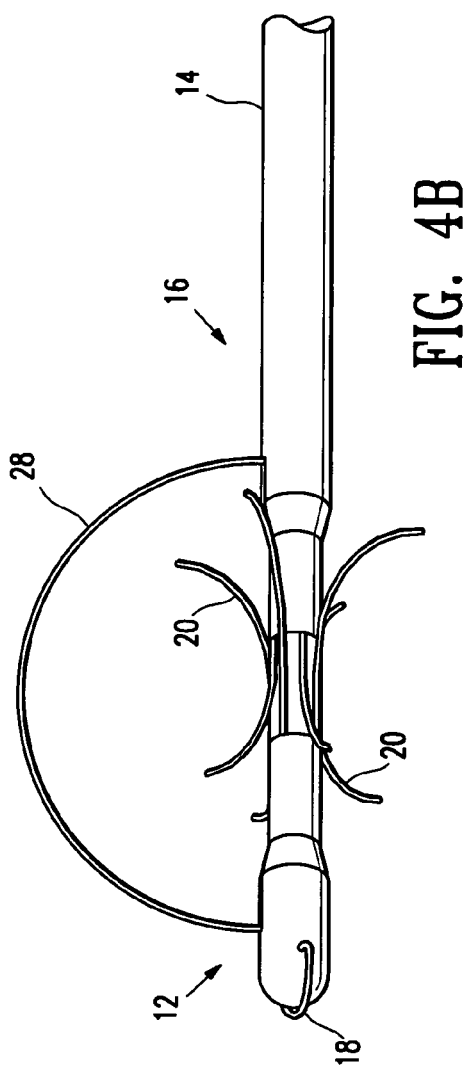
FIGS. 4B and 4C are perspective views of the distal portion of the wand showing extended radial wires and an extended side-cutting electrode illustrating features of the invention.
Figure 4C:
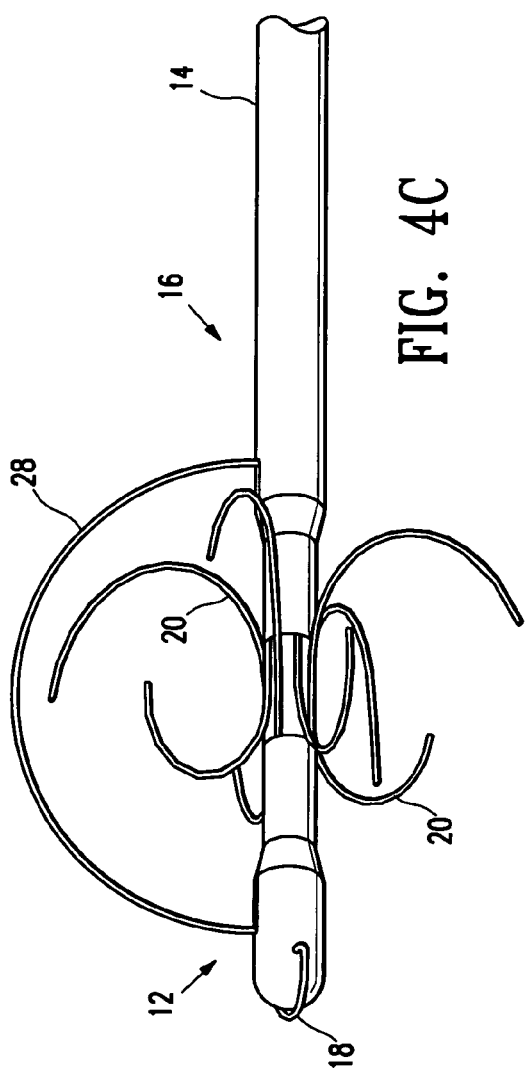
Figure 4A:
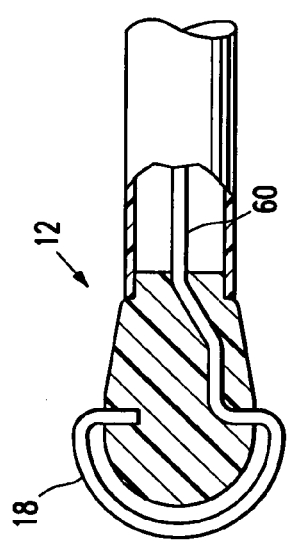
FIG. 4A is a partly cut-away perspective view of the distal tip of the wand particularly showing an electrosurgical electrode.

FIG. 4 shows the distal portion 16 of shaft 14 in a perspective view. FIG. 4A shows the electrosurgical electrode 18 in greater detail, providing a view of the interior of the distal tip 12 of wand 110 which allows a view of those portions of the electrosurgical electrode 18 positioned inside the distal tip 12. The electrosurgical electrode 18 as shown in FIG. 4 is a loop of conductor, such as stainless steel, which is operably connected to the distal end of conductor 60 providing electrical connection with, for example, a source of RF power 34. FIG. 4B illustrates the distal portion 16 of a shaft 14 of a device of the invention with an anchoring mechanism comprising radial wires 20. FIG. 4C illustrates the distal portion 16 of a shaft 14 of a device of the invention with an ablation mechanism comprising radial wires 20. Note that radial wires 20 shown comprising an ablation mechanism shown in FIG. 4C may be longer than the radial wires comprising an anchor mechanism shown in FIG. 4B. Also shown is a side-cutting electrode 28 and an electrosurgical electrode 18.

In their retracted configuration, shaft 14 of wand 110 houses the elements radial wires 20 (and may optionally house side-cutting electrode 28 where shaft 14 is provided with a side-cutting electrode slot), provides electrical connection between these elements and RF power source 34, and provides mechanical control effective to deploy these elements when it is desired to extend them outside slots 22 (and optionally, a side-cutting electrode slot). FIG. 5 provides cross-sectional views of the shaft 14 of wand 110 showing radial wires 20 housed within slots 22, with tips 56 of radial wires 20 within slots 22 in FIG. 5A (where radial wires 20 are shown in their retracted configuration) and extending out of slots 22 in FIG. 5C (where radial wires 20 are shown in their extended configuration). Transverse cross-sectional views of a shaft 14 of a wand 110 of the invention are shown in FIGS. 5B, 5D, 5E and 5F.

Figure 5D:
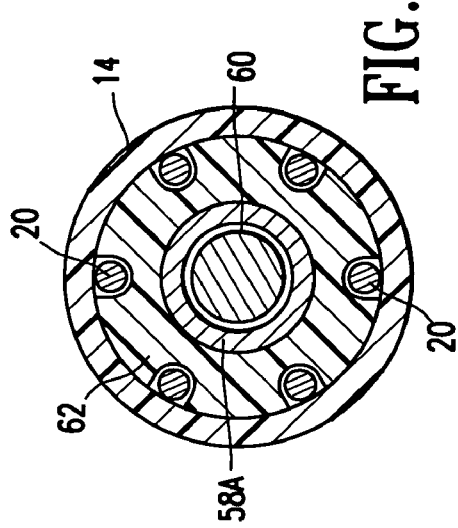
FIGS. 5B, and 5D-F are transverse cross-sectional views of the shaft of the wand of FIG. 1 embodying features of the invention.
Figure 5B:
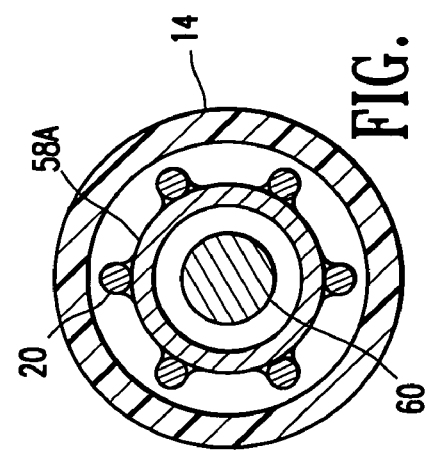
Figure 5F:
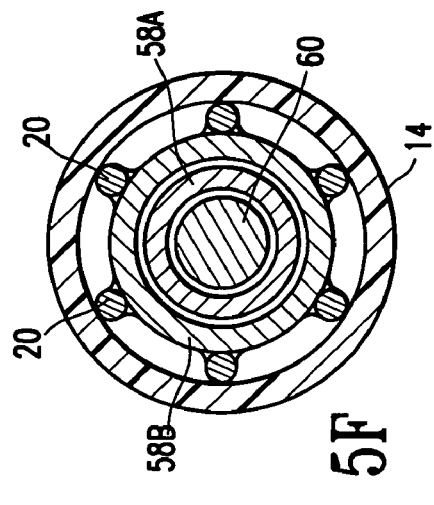
Figure 5E:
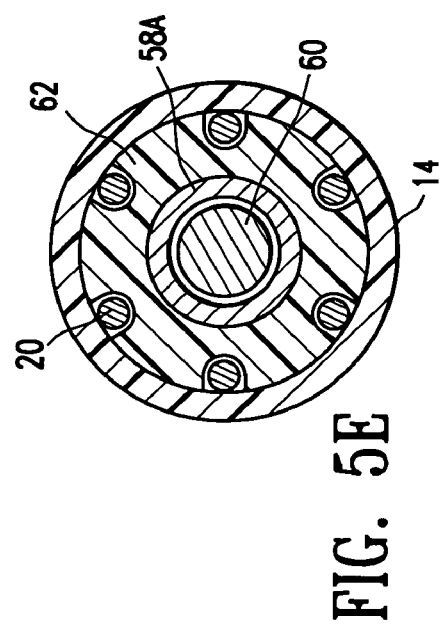

Slots 22 are in part defined by slot material 62, whereby radial wires 20 are able to slide within and exit from slots 22 during deployment. The radial wires 20 are shown retracted in FIGS. 5A, 5B and 5D-F. Radial wires 20 are operably connected to deployment shafts 58A and 58B, so that longitudinal motion of 58A in one direction, and longitudinal motion of 58B in the opposite direction, is effective to cause radial wires 20 to move within slots 22. As shown in FIG. 5C, longitudinal motion of deployment shafts 58A and 58B carries radial wires 20 effective to extend radial wires 20 out of slots 22. In preferred embodiments, anchor wires 20 have sharpened tips. In embodiments where radial wires 20 are effective to conduct RF energy to body tissues when the radial wires 20 are deployed and in contact with body tissues, deployment shafts 58A and 58B comprise conductors effective to conduct RF energy to radial wires 20. In embodiments, deployment shafts 58A and 58B may be insulated; in addition, deployment shafts 58A and 58B may comprise lubricating coatings or low-friction materials or coatings, such as may be provided by materials such as Teflon®. In most preferred embodiments, such insulation provides a low friction surface. Also shown in FIG. 5 is conductor 60, which extends within shaft 14 effective to provide electrosurgical electrode 18 with RF power. In preferred embodiments, conductor 60 is insulated; most preferably conductor 60 is insulated by insulation 61 effective to prevent electrical contact with deployment shafts 58A or 58B.

Figure 6A:
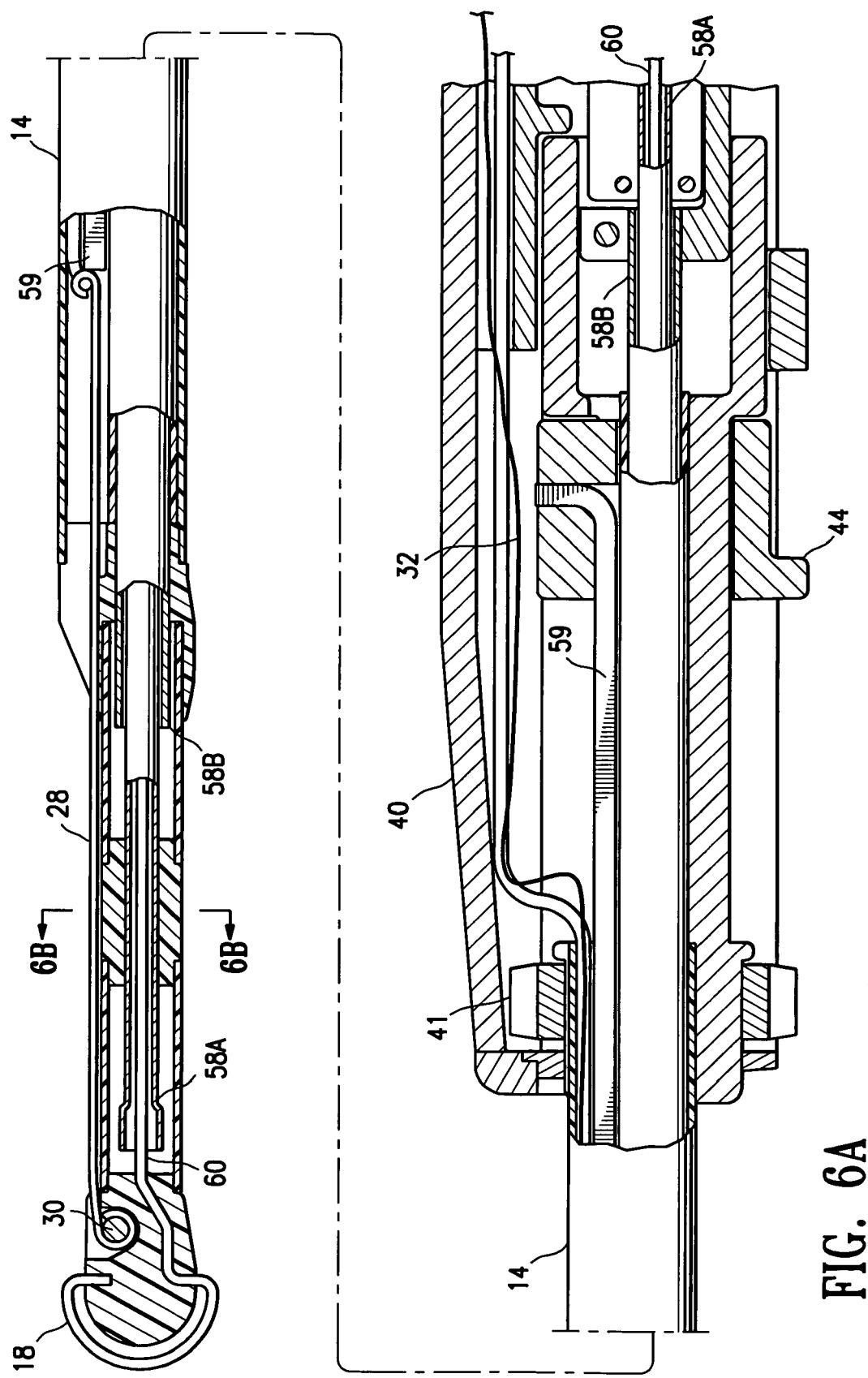

FIG. 6 provides partly cut-away views of the shaft 14 of a wand 110 of the invention showing the side-cutting electrode 28 in its retracted (6A, 6B) configuration, and in an extended configuration (6C, 6D). Side-cutting electrode 28 contacts push bar 59, which is preferably sufficiently rigid to effectively transmit mechanical force, extends within shaft 14 to contact side-cutting electrode shuttle 44 within housing 40 of wand 110. Preferably, push bar 59 is rigid, not conductive, and effective to move and position side-cutting electrode 28, while a conductor 32, separate from push bar 59, is used to supply RF power to side-cutting electrode 28. For example, in preferred embodiments push bar 59 may comprise a polyester push bar 59 while a conductor 32, e.g., preferably comprising Litz wire, provides electrical connection to side-cutting electrode 28. In alternative embodiments of the invention, push bar 59 is conductive effective to conduct RF energy to side-cutting electrode 28 without need for conductor 32. Longitudinal motion of the side-cutting electrode shuttle 44, as shown by the different positions of shuttle 44 in FIGS. 6A and 6C, is effective to urge push bar 59 and side-cutting electrode 28 in the same longitudinal direction. However, longitudinal motion of the side-cutting electrode is constrained by distal pivot 30, so that continued motion of side-cutting electrode shuttle 44 at one end, coupled with an inability for further longitudinal movement of side-cutting electrode 28 at the opposite end, causes side-cutting electrode 28 to bulge and extend radially outward to deploy along an arcuate path as shown in FIG. 6C. The radial movement of side-cutting electrode 28 is also shown, in transverse cross-sectional views, in FIGS. 6B and 6D. It will be understood by one of ordinary skill in the art that other embodiments of a deployment mechanism for side-cutting electrode 28, and of push bar 59 and conductor 32 connecting to side-cutting electrode 28, may be suitable for the practice of this invention. For example, in some embodiments side-cutting electrode 28 and push bar 59 may comprise a single continuous unit. In other embodiments, side-cutting electrode 28 is comprised of a memory metal, such as nitinol, effective to aid in the deployment of side-cutting electrode 28 upon provision of conditions triggering shape change in the memory metal.

Conductor 32 and conductor 60 (and, optionally, deployment shafts 58A and 58B and push bar 59) comprise conductors which run along a longitudinal axis of shaft 14 to provide electrical connection between a source of RF power 34 and the electrosurgical electrode 18 at the distal tip 12 of shaft 14, the side-cutting electrode 28 and optionally the radial wires 20. These electrical conductors operably connect to a source of electrical power, such as RF power source 34, of a type commonly used in electrosurgery. In preferred embodiments, the electrical conductors are insulated to maintain electrical isolation from adjacent components. For example, conductor 60 may be covered or enclosed by insulation 61. The electrical conductors may comprise the same or different conductors for connecting to each of the electrosurgical electrode 18, radial wires 20, and side-cutting electrode 28. For example, in an embodiment of the present invention wherein the electrosurgical electrode 18 and the radial wires 20 receive RF power at a frequency of 0.8 MHz, and the side-cutting electrode 28 receives RF power at a frequency of 5 MHz, conductors 58A, 58B and 60 would separately provide 0.8 MHz RF power to the electrosurgical electrode and radial wires and a conductor 32 would separately provide 5 MHz RF power to the side-cutting electrode 28.

At least a portion of conductors 32, 58A, 58B, 59 and 60 may comprise a flexible wire, more particularly conductors 58A and 58B connecting the anchoring mechanism or ablating mechanism, e.g. radial wires 20, conductor 32 and optionally push bar 59 connecting side-cutting electrode 28 to the RF power source 34. Flexible wire conductors are able to maintain electrical contact as the elongated shaft 14 is rotated, and as the anchoring mechanism or ablating mechanism (shown here as radial wires 20) and side-cutting electrode 28 are deployed. In a preferred embodiment, conductors such as 32, 58A, 58B, 59 and 60 are adapted to carry RF power efficiently by impedance matching, low capacitance, or other electronic design feature known in the art.

Figure 7:
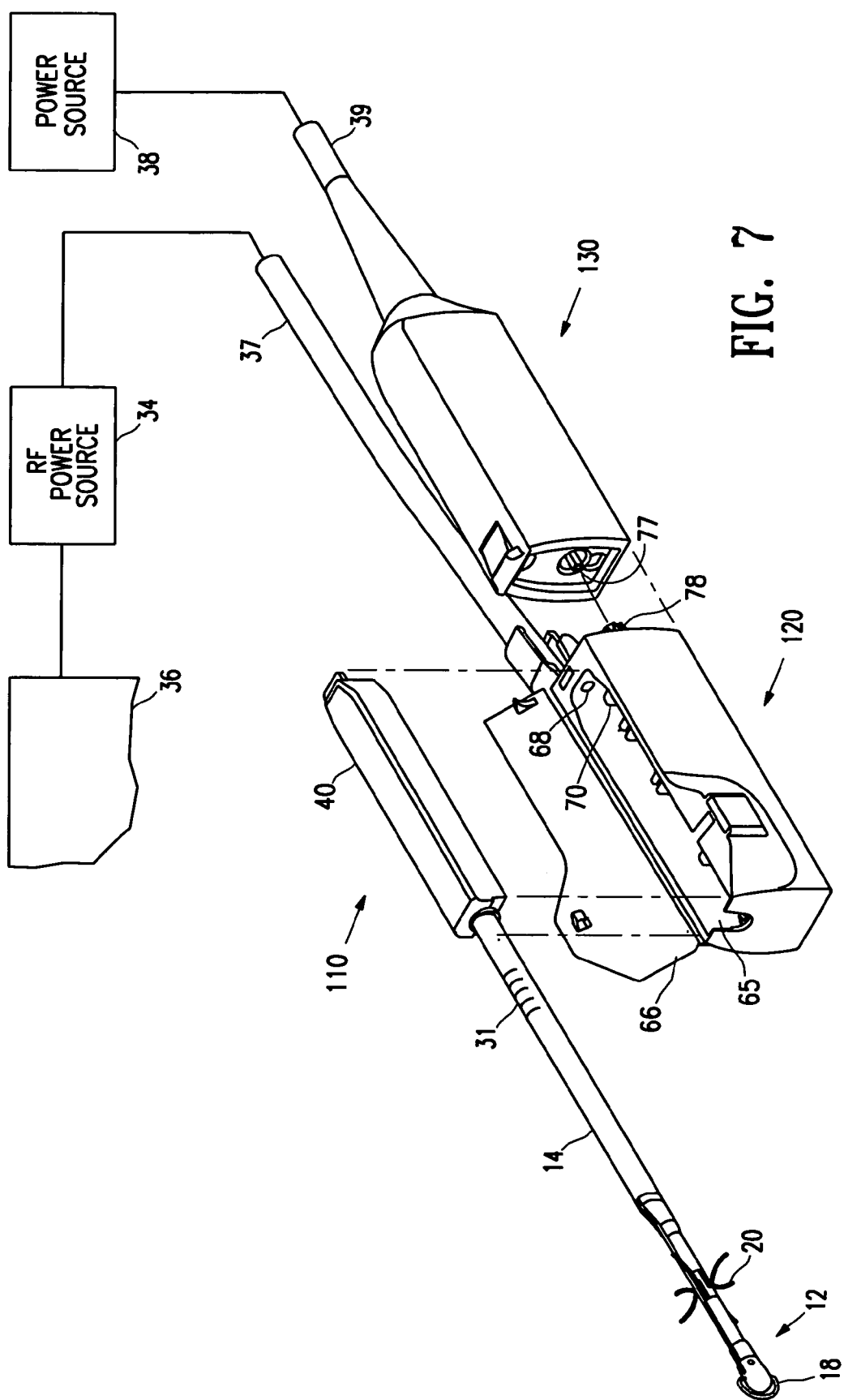
FIG. 7 is a perspective view of devices illustrating features of the invention.

System 10 of the invention may be assembled by assembly of the constituent parts, comprising wand 110, surgeon's disposable unit 120, and motor unit 130. As illustrated in FIG. 7, surgeon's disposable unit 120 and motor unit 130 snap together to form a mechanically stable unit whereby motive power may be transferred from motor unit 130 to surgeon's disposable unit 120. In preferred embodiments, the motive power is rotary power, with coupling between motor unit 130 and surgeon's disposable unit 120 provided by a shaft rotation assembly. In preferred embodiments, the shaft rotation assembly comprises a female part, such as a ridged sleeve 77 in motor unit 130, operably coupled to a motor or other source of rotary power, and a male part, such as spindle 78. In preferred embodiments, ridged sleeve 77 is adapted to receive spindle 78 effective to transfer rotary motion from ridged sleeve 77 to spindle 78.

As illustrated in FIG. 7, which provides perspective views of devices of the invention, surgeon's disposable unit 120 and the motor unit 130 snap together to form an effective unit where the surgeon's disposable 120 is operably connected to the motor unit 130, as shown in FIG. 7B. Assembly of the complete system 10 is effected by opening lid 66 and seating wand 110 in receptacle 65 within surgeon's disposable unit 120 (as shown in FIG. 7 illustrating the positions of the elements just prior to seating wand 110). Electrical connection is provided between wand 110 and RF power source 34 by means of electrical connector 68 in receptacle 65 of surgeon's disposable unit 120, while mechanical power is provided to wand 110 via shaft connector 70 within receptacle 65 of surgeon's disposable unit 120.

Figure 8A:
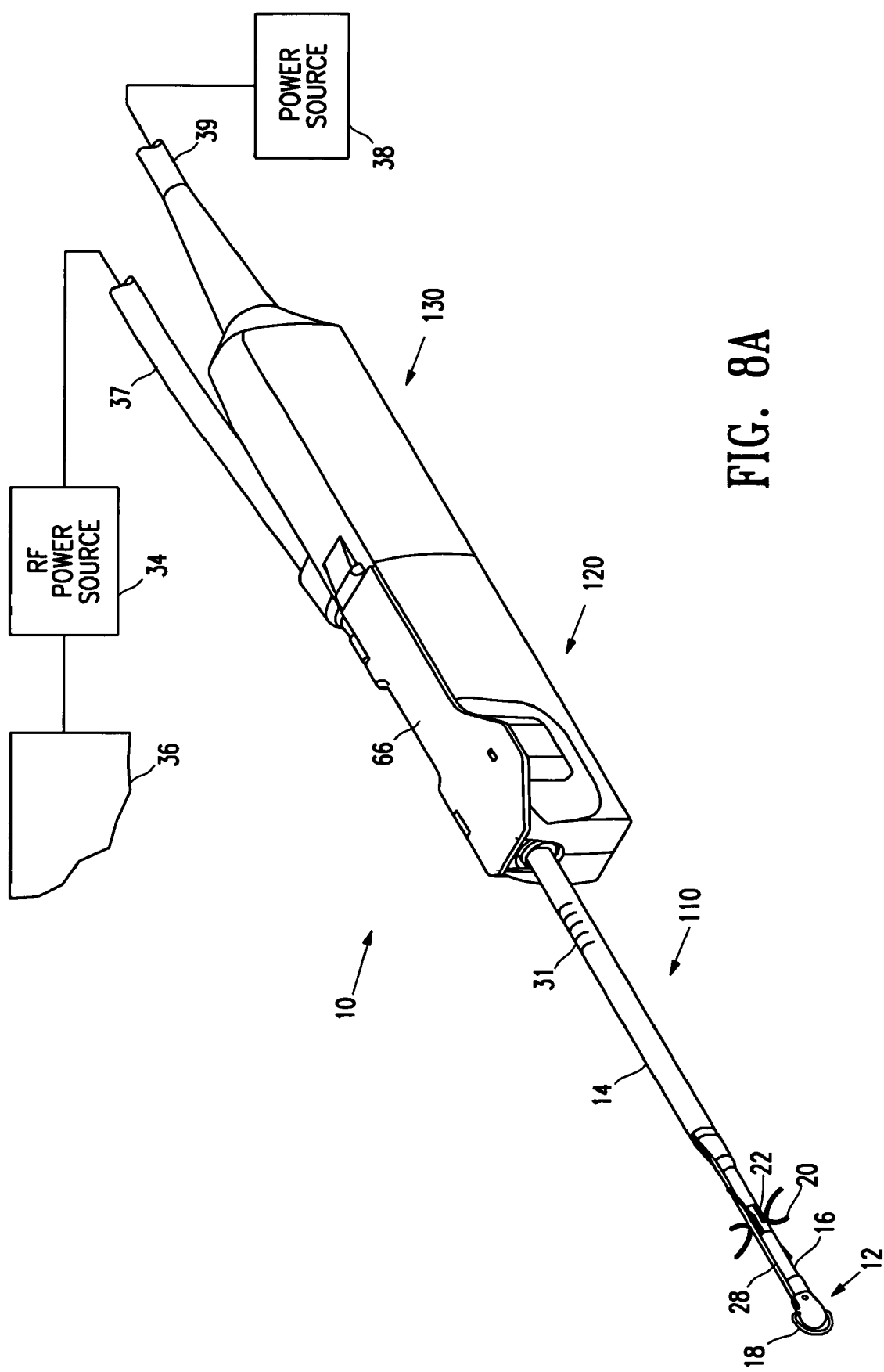
Figure 8B:
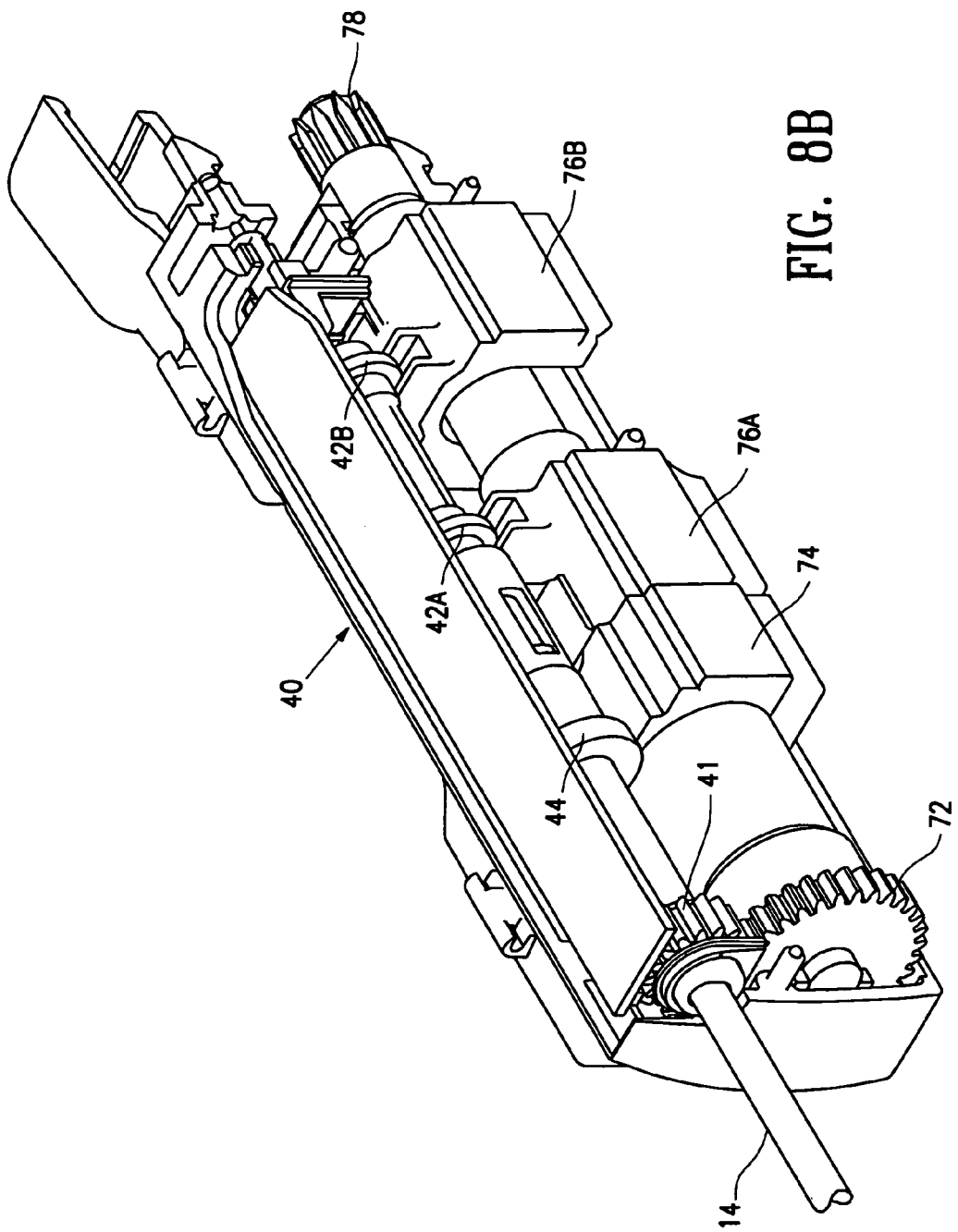

The assembled system 10 is shown in FIG. 8A, where shaft 14 extends out of surgeon's disposable unit 120, the rest of wand 110 being captured within receptacle 65 of surgeon's disposable unit 120, not shown in FIG. 8A because it is covered by lid 66. The system 10 is shown with radial wires 20 deployed in FIG. 8A; FIG. 8B shows the placement of electrode shuttles 44 (side-cutting electrode shuttle), and 42A and 42 B (radial wire shuttles) and drive elements 74 (side-cutting electrode shuttle clasp) and 76A and 76B (radial wire shuttle clasps) for the corresponding configuration of the device illustrated in FIG. 8A. Clasps 74, 76A and 76B engage shuttles 44, 42A, and 42B respectively as illustrated in FIG. 8A and are effective to move the shuttles 44, 42A, and 42B longitudinally to deploy or retract side-cutting electrode 28 and radial wires 20. It will be understood that the drive elements 74, 76A and 76B will assume different positions, corresponding to the configurations of the electrode shuttles 42A, 42B, and 44 shown in the Figures, in order to move the electrode shuttles 42A, 42B, and 44 so as to effect the deployment or retraction of side-cutting electrode 28 and radial wires 20.

The positions of the shuttles 44 (side-cutting electrode shuttle), and 42A and 42 B (radial wire shuttles) in the different configurations of electrode deployment are shown in FIGS. 8C-8F. The positions of the drive elements 74 (side-cutting electrode shuttle clasp) and 76A and 76B (radial wire shuttle clasps) also shown in these configurations, correspond to the positions of the shuttles since the shuttle-clasp drive elements engage the electrode shuttles at all times while the wand 110 is mounted within surgeon's disposable unit 120.

The positions of electrode shuttles 44, 42A and 42B and shuttle clasps 74, 76A and 76B are shown in FIG. 8C for the configuration in which the side-cutting electrode and the radial wire electrodes are retracted. Separation of the radial wire electrode shuttles 42A and 42B, as indicated by the arrows in FIGS. 8C and 8D, is effective to deploy the radial wire electrodes 20 as illustrated in FIG. 8D. Such separation may be effected by separation of the radial wire electrode shuttle clasps 76A and 76B as shown in FIG. 8D.

Deployment of the side-cutting electrode 28, as illustrated in FIG. 8E, is effected by longitudinal movement of the side-cutting electrode shuttle 44, as indicated by the arrow near to side-cutting electrode shuttle 44 in FIG. 8E. Deployment of the side-cutting electrode 28 itself is indicated in FIG. 8E by the radial arrow shown pointing to the deployed side-cutting electrode 28; such deployment may be effected by longitudinal movement of side-cutting electrode shuttle clasp 74 as shown in FIG. 8E. It will be understood that retraction of the side-cutting electrode 28 may be effected by movement of the side-cutting electrode shuttle clasp 74 and side-cutting electrode shuttle 44 in the opposite direction.

Retraction of the radial wire electrodes 20 is effected by movement together of the radial wire electrode shuttles 42A and 42B, as illustrated in FIG. 8F, with arrows indicating the direction of movement that resulted in the final position of the radial wire electrode shuttle clasps 76A and 76B and radial wire electrode shuttles 42A and 42B shown in the figure. Longitudinal arrows near the radial wire electrodes 20 indicate the direction of movement of the radial wire electrodes themselves during retraction.

Thus, in preferred embodiments, the deployment and retraction of radial wires 20 and of side-cutting electrode 28 may be effected by the mechanisms illustrated in FIG. 8. When seated in receptacle 65, wand 110 is placed so as to engage side-cutting electrode shuttle 44 with side-cutting electrode shuttle clasp 74, and radial wire shuttles 42A and 42B are placed so as to engage radial wire shuttle clasps 76A and 76B. Note that when side-cutting electrode 28 is retracted as in FIGS. 8A-8D; side-cutting electrode shuttle clasp 74 is positioned away from drive gear 72, in the most proximal position along its range of motion. In FIGS. 8E and 8F, the side-cutting electrode 28 is deployed. In this configuration side-cutting electrode shuttle clasp 74 is in its most distal position. Movement of side-cutting electrode shuttle clasp 74 in a distal direction, when engaged with side-cutting electrode shuttle 44, is effective to deploy side-cutting electrode 28.

Similarly, radial wires 20 are shown deployed in FIGS. 8A and 8D, and retracted in FIG. 8C. In this configuration, radial wire shuttle clasps 76A and 76B are laterally displaced from each other, as shown in FIG. 8B. When engaged with radial shuttles 42A and 42B, radial shuttle clasps 76A and 76B are effective to deploy radial wires 20 when positioned lateral from a medial position at which the radial wires 20 are retracted.

Shaft 14 may be rotated by rotation of drive gear 72 which is operably engaged with shaft gear 41. When such rotation is effected while side-cutting electrode 28 is deployed and conducting RF power into a patient's tissues, a swath of tissue will be cut or ablated. In preferred embodiments, the rotary motion comprises at least 360°, or a complete circle, effective to completely isolate a body of tissue within the patient's body. In most preferred embodiments, the rotary motion comprises at least 360° plus about 45°, or about 405°, effective to completely isolate a body of tissue within the patient's body and to leave the side-cutting electrode 28 in a position that is not above the slot in the tissue that is formed by deployment of the side-cutting electrode 28. Removal of such an isolated body of tissue then provides a biopsy specimen or may comprise a surgical procedure, such as a lumpectomy. Referring to FIG. 8, the system 10 is shown ready to begin a procedure in FIG. 8A, with shaft 14 anchored in position in a patient's body by radial wires 20. Retraction of radial wires 20, and deployment of side-cutting electrode 28, preferably with RF power supplied to side-cutting electrode 28, is shown in FIG. 8F. Retraction of radial wires 20 facilitates rotation of shaft 14 and aids cutting by side-cutting electrode 28. hen shaft 14 is in place within a patient's body, rotation of shaft 14 with side-cutting electrode deployed and supplied with RF power is effective to cut and isolate a body of tissue within a patient's body. Following such cutting and isolation of tissue, side-cutting wire 28 may be retracted and radial wires 20 redeployed, as in the configuration shown in FIG. 8D, fixing the isolated body of tissue to shaft 14 for removal of the body of tissue when shaft 14 is removed from the patient.

Figure 9:
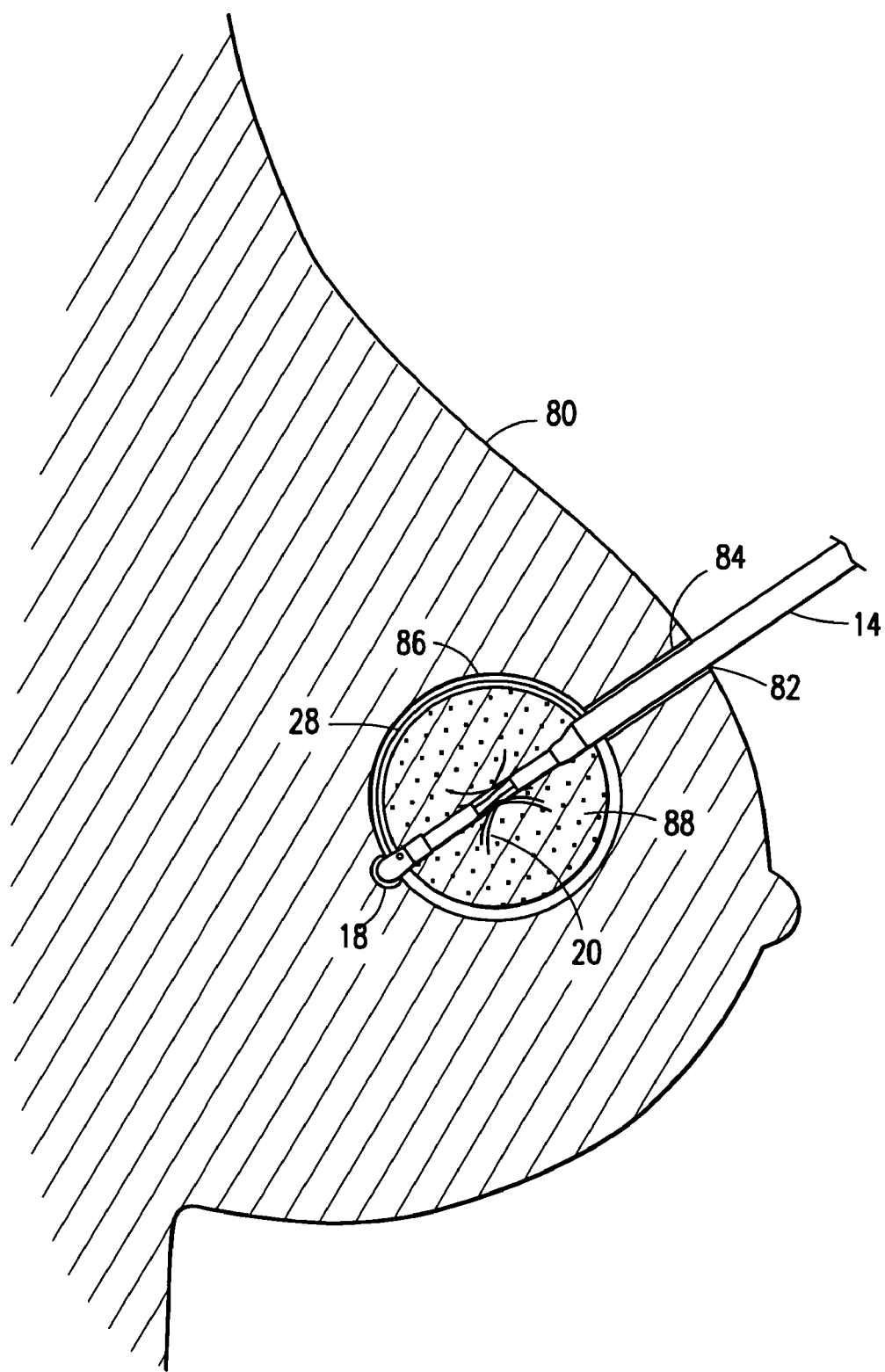
FIG. 9 is a cross-sectional view of a breast of a patient undergoing a clinical procedure embodying features of a method of the invention, showing a distal portion of a device embodying features of the invention.

An illustration of a portion of the device positioned within the body of a patient is provided in FIG. 9. In preferred embodiments, the invention will be used to perform biopsies, lumpectomies, and other procedures on the breast tissue of patients. FIG. 9 shows a cross-sectional view of a breast 80 of a patient undergoing a clinical procedure comprising an embodiment of a method of the invention, showing a portion of a shaft 14 with an electrosurgical electrode 18 at the distal tip. The shaft 14 has been inserted in the breast 80 through an incision 82 in the surface of the breast 80, along a path 84 created by action of the electrosurgical electrode 18 under the guidance of an operator, such as a surgeon. Prior to the configuration illustrated in FIG. 9, radial wires 20 had been deployed to anchor the wand 110 in a desired location, then had been retracted prior to rotation of shaft 14. Next, side-cutting electrode 28, shown here in its deployed configuration, was used to make a boundary cut 86 within the breast 80 of the patient, effective to isolate a body of tissue 88 within the boundary cut 86. The isolated tissue is fixed in position around shaft 14 by radial wires 20, which were preferably redeployed after side-cutting electrode 28 made boundary cut 86. In preferred embodiments, the side-cutting electrode 28 would next be at least partially retracted, while the radial wires 20 remain deployed with isolated tissue 88 attached to the radial wires 20. Removal of the device by pulling the device back along path 84 is effective to remove isolated tissue 88.

FIG. 10 illustrates rotation of the shaft 14 and side-cutting electrode 28 during isolation of a body of tissue within a patient's body. FIGS. 10A, 10B, and 10C illustrate transverse cross-sections taken along line C-C depicted in FIG. 10D, which is a partially cut-away cross-sectional view of a wand 110 of the invention. As illustrated in FIG. 10A, side-cutting electrode 28 has been deployed, and radial wire electrodes 20 have been retracted. Rotation of shaft 14 and side-cutting electrode 28 around a longitudinal axis of the shaft 14 is indicated by the curved arrow in FIG. 10A. FIG. 10B depicts the position of the shaft 14 and side-cutting electrode 28 after a full rotation with RF power supplied to the side-cutting electrode 28. The body of target tissue 88 has been isolated from surrounding body tissue by boundary cut 86 formed by the passage of the side-cutting electrode 28 in the direction indicated by the curved arrow. Note that shaft 14 and side-cutting electrode 28 have rotated more than a full circle, through greater than 360°, leaving side-cutting electrode in a position away from the radial cut made as the side-cutting electrode 28 was deployed. Following formation of boundary cut 86 effective to isolate body of tissue 88, RF power was supplied to radial wire electrodes 20 which are deployed as shown in FIG. 8C in order to fix body of tissue 88 in position along the shaft. The position of radial wire shuttles 42A and 42B in this configuration is shown in FIG. 10D, with longitudinal arrows indicating the direction of travel of radial wire shuttles 42A and 42B. In addition, RF power is shut-off from side-cutting electrode 28 at this point; and it may be retracted, partially or completely, as illustrated in FIG. 10C, to aid in fixing the body of tissue 88 to the shaft; alternatively, side-cutting electrode may be left deployed. With body of tissue 88 fixed to shaft 14 by radial wire electrodes 20 and optionally by side-cutting electrode 28, the body of tissue 88 may be withdrawn from the patient's body.

The devices of the invention, when inserted into a patient's tissue at the appropriate position, provide access to a desired site or a target tissue site under examination. The pathway produced in reaching the desired site in the patient's tissues, provides access for directing fluid, gel, paste, chemicals, drugs, markers, or other fluid or semifluid material to the region of the patient's body. Devices of the invention may themselves provide means to introduce markers, chemicals, drugs, fluids or other objects to the desired site in the patient. U.S. patent application Ser. No. 09/343,975 (assigned to the assignee of the present application and herein incorporated by reference in its entirety) describes the use of such temporary and permanent markers, and its disclosure is incorporated herein by reference. For example, a surgical dye may be injected along the elongated shaft 14 or a surgical dye may be injected through a bore provided in shaft 14 to mark the region and to provide a guide for subsequent surgical procedures. Also, hemostatic agents (such as those that contain fibrin or a fibrin/fibrinogen mixture) may be introduced along the elongated shaft 14 or through a bore provided in shaft 14 to stem bleeding that may occur during a biopsy procedure.

The use of devices of the invention, and methods for accessing tissue at a desired site within a patient and isolating a body of target tissue, methods for performing a biopsy, and methods for performing a lumpectomy, are provided in more detail in the following paragraphs.

Typically, an incision is first made (e.g., with a conventional scalpel) through the patient's skin. With RF power supplied to the electrosurgical electrode 18, the electrosurgical electrode 18 and the distal tip 12 of the wand 110 are inserted into the incision. In accordance with the use of conventional electrosurgical apparatus, the operator activates an electrosurgical generator (such as the source of RF power 34) using a control switch (not shown), such as a foot pedal, to apply high frequency electrical energy to the electrosurgical electrode 18. In embodiments of the invention, the electrosurgical generator can operate at about 100 KHz (0.1 MHz) to about 10 MHz. In one embodiment of the invention, the electrosurgical generator can operate at about 300 KHz to about 1500 KHz (1.5 MHz), specifically, at about 600 KHz to about 1000 KHz (1 MHz), most preferably about 800 KHz (0.8 MHz). Power output for such an electrosurgical generator can be about 50 to about 150 watts, preferably, about 80 to about 100 watts. Where tissue coagulation is desired, greater amounts of power output may be supplied, and/or the waveform may be changed, and/or the voltage increased. As the electrosurgical electrode 18 contacts the tissue, the contacted tissue is ablated, allowing insertion of the electrosurgical electrode 18 and shaft 14 through the tissue without deforming or displacing tissue it is passing through.

The electrosurgical electrode 18 makes a passage through the tissue that permits shaft 14 to be readily inserted, providing a suitable passage through the tissue without pushing tissue aside or displacing target tissue as it advances. The electrosurgical ablation process is continued until the electrosurgical electrode 18 and shaft 14 are appropriately positioned with regard to the desired site within the patient's body. Once in place, the electrosurgical electrode 18 and shaft 14 provide access to the desired site within the patient's body.

In order to prevent movement of shaft 14 after placement in the desired site within the patient's body, radial wires 20 may be extended, penetrating tissue in a generally radial direction away from shaft 14 of the wand 110. The radial wires 20 penetrate into the tissue as they extend, and are effective to prevent undesired movement and to anchor shaft 14 in place. It will be understood by those of skill in the art that wires, such as radial wires 20, will readily penetrate into a patient's tissues without displacing or deforming surrounding tissues. In a preferred embodiment, RF power is supplied to the radial wires 20 as they are extended, so that the radial wires 20 cut through a patient's tissues quite readily so as to penetrate into a patient's tissues without displacing or deforming surrounding tissues. In accordance with the use of conventional electrosurgical apparatus, the operator activates an electrosurgical generator (such as the source of RF power 34) using a control switch (not shown), such as a foot pedal, to apply high frequency electrical energy to the radial wires 20. In embodiments of the invention, the electrosurgical generator can operate at about 100 KHz (0.1 MHz) to about 10 MHz. In one embodiment of the invention, the electrosurgical generator (such as RF power source 34) can operate at about 300 KHz to about 1500 KHz (1.5 MHz), specifically, about 600 KHz to about 1000 KHz (1 MHz), most preferably about 800 KHz (0.8 MHz). Power output for such an electrosurgical generator can be about 50 to about 150 watts, preferably, about 80 to about 100 watts. Where tissue coagulation is desired, greater amounts of power output may be supplied. As the radial wires 20 contact the tissue, the contacted tissue is ablated, allowing extension of the radial wires 20 through the tissue without causing undesired motion of the wand 110 and without deforming or displacing the surrounding tissue. In the extended configuration, the radial wires 20 anchor the electrosurgical system 10 into place, preventing motion or displacement from the desired site. As can be seen from the two depictions of the radial wires 20 in FIG. 4, the amount of extension of the radial wires 20 may vary, either depending upon their intended use (as anchor wires or as ablation wires, for example) or the extent of deployment may be controlled as desired by the operator, with movement of the radial wires 20 effected by action of deployment shafts 58A and 58B. The radial wires may be completely housed within shaft 14, as is desirable, for example, during the initial insertion of wand 110 and passage through the tissues of the patient before arrival at the final desired site within the patient's body.

In preferred embodiments, side-cutting electrode 28 lies along shaft 14 when not deployed. In alternative embodiments, side-cutting electrode 28 may be housed in shaft 14, and of being extended in a substantially radial direction to deploy from a slot to form an arcuate electrode.

During deployment of the side-cutting electrode 28, RF power may be supplied to the side-cutting electrode 28 to facilitate its travel through the patient's tissues. In accordance with the use of conventional electrosurgical apparatus, the operator activates an electrosurgical generator (such as the source of RF power 34) using a control switch (not shown), such as a foot pedal, to apply high frequency electrical energy to the side-cutting electrode 28. In embodiments of the invention, the electrosurgical generator can operate at about 100 KHz (0.1 MHz) to about 10 MHz. In one embodiment of the invention, the RF power source 34 can operate at about 500 KHz to about 10,000 KHz (10 MHz), preferably, about 2500 KHz to about 7500 KHz (about 2.5 MHz to about 7.5 MHz), most preferably about 5000 KHz (5 MHz). Power output for such an electrosurgical generator can be about 100 to about 1000 watts, preferably, about 120 to about 500 watts. Where tissue cauterization is desired, greater amounts of power output may be supplied. As the side-cutting electrode 28 contacts the tissue, the contacted tissue is ablated, allowing extension of the side-cutting electrode 28 through the tissue without causing undesired motion of the shaft 14 or of wand 110 and without deforming or displacing the surrounding tissue. The side-cutting electrode 28 is effective to cut tissue and also to cauterize tissue when a suitable amount of RF power is supplied to the side-cutting electrode 28.

The side-cutting electrode 28 may be used to cut a path through tissue effective to isolate a portion of the body tissue of a patient. When the shaft 14 is in a desired site within a patient's body, tissue that is the object of interest, such as tissue to be taken for a biopsy sample, is located adjacent or near to shaft 14. The side-cutting electrode 28 may be deployed to a variable extent, that is, to a greater or lesser maximal radial distance from shaft 14 as desired by the operator. A desired maximal radial distance is one where the radius of the arc of the side-cutting electrode 28 is greater than the distance of the tissue of interest from shaft 14, and, when rotated around longitudinal axis 24, defines a shape that is substantially a spheroid enclosing the tissue of interest. Application of RF power to the side-cutting electrode 28, retraction of the radial wires 20 and rotation of the side-cutting electrode 28 around longitudinal axis 24 is effective to cut a substantially spherical or ellipsoidal passageway to form boundary cut 86 through a portion of the patient's body tissue. Such rotation of the side-cutting electrode 28 around longitudinal axis 24 while the side-cutting electrode 28 is deployed and connected to and receiving RF power, with radial wires 20 retracted, is effective to provide boundary cut 86 within the patient's body, effective to isolate the tissue of interest 88 from body tissue that is located farther from shaft 14 than the side-cutting electrode 28. The power supplied to the side-cutting electrode 28 may be sufficient to cut tissue or greater power may be used effective to coagulate the tissue adjacent boundary cut 86 that is cut by the side-cutting electrode 28. As disclosed above, preferred RF power for the side-cutting electrode 28 is supplied by RF power source 34 preferably at a frequency of about 5 MHz, although RF power in a frequency range of between about 2.5 MHz to about 7.5 MHz, and in a range of between about 0.1 MHz to about 10 MHz is also within the scope of the invention.

In addition to wand 110, surgeon's disposable unit 120, motor unit 130, and manual handle 140, the invention comprises methods of accessing target tissue, and of isolating tissue, of performing a biopsy on target tissue at a desired site within a patient, and of performing a lumpectomy on a breast of a patient.

A method of accessing target tissue at a desired site within a patient's body comprises providing an electrosurgical device or wand 110, positioning the electrosurgical electrode 18 of the device 110 in contact with the patient's body, supplying high frequency electrical current to the electrosurgical electrode 18 while advancing the distal end 16 of the device 110 into the patient and through the site of target tissue, expanding the elongated members of an anchoring mechanism (preferably radial wires 20) to penetrate the surface of the target tissue in order to fix the device 110 with respect to the target tissue site, expanding the cutting element of the side-cutting mechanism 28 into the target tissue, and rotating the cutting element of the side-cutting mechanism 28 about a longitudinal axis 24 of shaft 14 of the device 110 to form a body of target tissue 88. In one embodiment of the method, the skin of the patient may be first cut to expose subcutaneous tissue before supplying high frequency electrical current to the electrosurgical electrode 18 while the electrosurgical electrode 18 is advanced through the tissue of the patient.

A method of performing a biopsy on target tissue at a desired site within a patient comprises providing a device 110 of the invention, positioning the electrosurgical electrode 18 in contact with the patient's body, supplying high frequency electrical current to the electrosurgical electrode 18 while advancing the distal end 16 of the device 110 into the patient and through the site of target tissue, expanding the elongated members of the anchoring mechanism, such as radial wires 20, to penetrate the surface of the target tissue in order to fix the device with respect to the target tissue site, expanding the cutting element of the side-cutting electrode 28 into the target tissue, rotating the cutting element of the side-cutting electrode 28 about a longitudinal axis 24 of the shaft 14 of the device 110 to form a body of target tissue 88, and withdrawing the biopsy device 110 with the body of target tissue 88 from the patient.

A method of performing a lumpectomy on a breast of a patient comprises providing a device of the invention 110, positioning the electrosurgical electrode 18 of the device 110 in contact with the patient's breast tissue, supplying high frequency electrical current to the electrosurgical electrode 18 while advancing the distal end 16 of the device 110 into the patient's breast tissue and through the site of target tissue, expanding the elongated members of the anchoring mechanism, such as radial wires 20, to penetrate the surface of the target tissue in order to fix the device with respect to the target tissue site, expanding the side-cutting electrode 28 of the side-cutting mechanism into the target tissue, rotating the side-cutting electrode 28 of the side-cutting mechanism about a longitudinal axis 24 of shaft 14 of the device 110 to form a body of target tissue 88, and withdrawing the device 110 and the body of target tissue 88 from the patient's breast.

In the practice of these methods, including the method of performing a biopsy on target tissue at a desired site within a patient and the method of performing a lumpectomy on a breast of a patient, the electrical current supplied to the electrosurgical electrode may be at a frequency of about 0.1 MHz to about 10 MHz; more preferably about 0.3 to about 1.5 MHz, and most preferably at a frequency of about 0.8 MHz. The elongated members of the anchoring mechanism, such as radial wires 20, may be formed of electrically conducting material and high frequency electrical current is preferably supplied to the elongated members of the anchoring mechanism while they penetrate the surface of the target tissue. In the practice of the methods, the electrical current supplied to the radial wires 20 may be at a frequency of about 0.1 MHz to about 10 MHz; more preferably about 0.3 to about 1.5 MHz, and most preferably at a frequency of about 0.8 MHz. The electrical current supplied to the side-cutting electrode 28 of the side-cutting mechanism may be supplied at a frequency greater than the frequency of the electrical current supplied to the electrosurgical electrode 18. In the practice of the methods, the electrical current supplied to elongated electrode of the side-cutting mechanism 28 may be at a frequency of about 0.1 MHz to about 10 MHz; more preferably about 2.5 to about 7.5 MHz, and most preferably at a frequency of about 5 MHz. The side-cutting electrode 28 of the side-cutting mechanism may be expanded to an arcuate shape that upon rotation about the axis 24 of the shaft 14 is effective to isolate a body of target tissue 88 that is spherical or substantially spherical. Following isolation of the target tissue 88, the radial wires 20 may again be deployed, fixing the target tissue 88 to the device 110 effective to remove the target tissue 88 along with the removal of the device 110 from the patient's body.

In a further embodiment of the invention, the shaft 14 of wand 110 may be withdrawn from the passage 84 that provides access to the desired site in the patient's body, and another device inserted into the passage. For example, a biopsy device may be inserted along the passage 84 to remove a biopsy sample. A biopsy device may be advantageously of the type described in U.S. Pat. Nos. 5,526,822; 5,649,547; 5,775,333; and 5,928,164, the disclosures of which are incorporated herein by reference. In preferred embodiments of the method in which a biopsy device is inserted along the passage, a biopsy device such as a Mammotome® with a sampling chamber, is inserted into the passage, so that the sampling chamber is aligned with the target tissue, until the sampling chamber of the biopsy device is exposed within the target tissue mass 88 and the biopsy sample taken. Alternatively, the wand 110 may comprise a biopsy device.

In addition, it is often desirable to place markers to identify the location from which biopsy samples were taken. The methods disclosed herein contemplate the use of such markers in conjunction and combination with other methods of the invention for accessing target tissue at a desired site within a patient and isolating a body of target tissue, for performing a biopsy on target tissue at a desired site within a patient, and for performing a lumpectomy on a breast of a patient. If tests on the sample indicate that surgery is called for to remove tissue from the biopsy site, the markers identify the location of the site using x-rays, ultrasound, or other imaging techniques, to permit the surgeon to remove the appropriate tissue. In some instances, it may be desirable to mark the location from which the biopsy samples were taken with a permanent marker. This may be appropriate when the examination determines that the tissue taken at the biopsy site was benign. Doctors may find it helpful to identify in subsequent examinations of the patient that the suspect tissue mass has previously been examined, and determined not to require further biopsy. Location markers for such purposes are typically permanent, but they may alternatively be temporary, designed to be absorbed into the body in a few weeks to a few months. Permanent markers may include metal clips that are visible with x-rays. Temporary markers may be formed of a biocompatible, radio-opaque gel that is absorbed over time in the body tissue. Both temporary and permanent markers are described in previously noted U.S. patent application Ser. No. 09/343,975, filed Jun. 30, 1999.

A marker insertion device for placing such markers may be guided through passage 84 created by wand 110 and used to install a permanent marker, such as, for example, a metal clip. Other devices or materials may be inserted into or through the passageway created by the use of wand 110. For example, a surgical dye and/or a hemostatic agent may be injected, as discussed above, or a coagulation device, such as the electrosurgical unit, may be inserted.

At the conclusion of all procedures requiring access to the desired site within a patient's body and the tissue surrounding it, the wand 110 may be removed from the patient's tissue, or, if another device or devices have been inserted into the passage 84 created by wand 110 after removal of wand 110, these devices are removed. The incision is then appropriately closed.

Those skilled in the art will recognize that various modifications may be made to the specific embodiments illustrated above without departing from the spirit of the present invention. For example, it will be understood that although radial wires 20 and side-cutting electrode 28 comprise preferred embodiments of anchoring mechanisms and side-cutting mechanisms of the invention, the invention is not intended to be limited to these embodiments alone, but to include variants and alternative embodiments as well, as one of ordinary skill in the art will appreciate that other embodiments of the anchoring mechanism and side-cutting mechanism, including alternative shapes of these elements, are also suitable for the practice of the invention. Such alternative embodiments of, for example, anchoring devices, may include hooks, barbs, fins, glues, and other means suitable to serve as an anchoring mechanism and are within the scope of the invention.

In addition, it will be recognized that additional steps may be added to the procedure described above, depending on the specific needs of the patient. These and other modifications that may suggest themselves are considered to be within the spirit and scope of the invention, as defined in the claims that follow.

What is claimed is:

1. A system for accessing target tissue within a patient and isolating a body of target tissue from its supporting bed, comprising a. a biopsy device having a wand with a proximal portion and a distal portion, a housing on the proximal portion, an electrosurgical tissue cutting electrode secured to the distal portion of the wand, a first electrical conductor extending within the wand having a distal end electrically connected to the electrosurgical electrode and a proximal end configured to be electrically connected to an electrical power source, at least one deployable tissue contacting element connected to said distal wand portion and at least one driving member within the housing configured to move at least one deployable tissue contacting element of the biopsy device;

b. a replaceable drive unit having a receptacle for engaging and releasably holding at least a portion of the housing on the proximal portion of the wand, and a driving element configured to engage the at least one driving member within the housing configured to transfer mechanical power to said biopsy device; and d. a motor unit for engaging and providing power to the driving element of the drive unit, comprising a securing mechanism effective to form a mechanically stable engagement between said motor unit and said drive element of the driving unit to transfer mechanical power therebetween.

2. The system of claim 1, wherein said at least one deployable element is a side-cutting element.

3. The system of claim 2, wherein the wand has a distal end and said side-cutting element is located proximal to the distal end of the wand.

4. The system of claim 3, wherein said side-cutting mechanism is configured to be rotated about a longitudinal axis of the wand to isolate a body of target tissue when said wand is disposed within a patient.

5. The system of claim 2, wherein said tissue anchoring mechanism comprises a radially extending wire.

6. The system of claim 2, wherein said anchoring mechanism of said biopsy device includes a plurality of elongated members configured to expand outwardly from the wand and to penetrate into target tissue.

7. The system of claim 6 wherein said elongated members of said anchoring mechanism are formed at least in part of electrically conducting material.

8. The system of claim 7 wherein a third electrical conductor extends within the elongated shaft of the biopsy device and has a distal end electrically connected to at least one of the elongated members and a proximal end configured to be electrically connected to an electrical power source.

9. The system of claim 7 wherein the elongated members of said anchoring mechanism are metallic wires or ribbons.

10. The system of claim 7 wherein the wires or ribbons are movably mounted to the wand of the biopsy device and have a contracted configuration to facilitate advancement of the biopsy device within the patient and a radially expanded configuration to penetrate into target tissue.

11. The system of claim 1 wherein the at least one deployable element is an anchoring mechanism which is configured to be extended into the body of target tissue when said wand is disposed within a patient.

12. The system of claim 11, including a side-cutting mechanism comprising an elongated electrode having a distal end secured distal to the anchoring mechanisms, a proximal end secured proximal to the anchoring mechanism and a second electrical conductor extending within the wand having a distal end electrically connected to the elongated electrode and a proximal end configured to be electrically connected to an electrical power source.

13. The system of claim 1, wherein the drive element of said drive unit is configured to engage a shuttle effective to deploy or retract the deployable element of said biopsy device.

14. The system of claim 1, wherein said drive unit further comprises a drive gear configured to engage a shaft gear effective to rotate said wand.

15. The system of claim 1, wherein said drive unit has a mechanical connector comprising a spindle, and wherein said transferred mechanical power comprises rotary power.

16. The system of claim 1, wherein said securing mechanism of said motor unit comprises a releasable connection.

17. The system of claim 1, wherein said mechanical power of said motor unit comprises rotary power and said securing mechanism comprises a ridged sleeve configured to receive a spindle effective to transfer rotary motion.

18. The system of claim 1, wherein said electrosurgical electrode of said biopsy device has a cutting surface spaced distal to the distal end of the shaft.

19. A system for severing a tissue body within a patient from supporting tissue, comprising:

a. a tissue severing unit having an elongated wand with a tissue cutting element on a distal portion of the wand, an additional operative element on the distal portion of the wand and a housing on a proximal portion of the wand and moving elements within the housing for moving the tissue cutting element and the additional operative element;

b. a replaceable drive unit having a recess for receiving at least a portion of the housing of the tissue severing unit and having driving elements for engaging moving elements within the housing of the tissue severing unit to operate the tissue cutting element and the additional operative element on the distal portion of the wand; and c. a motor unit having a motor, a mechanical connector configured to transfer mechanical power from the motor to the driving elements of the drive unit to operate the tissue severing element and to operate the additional operative element of the tissue severing unit.

20. The system of claim 19 including a securing mechanism effective to form a mechanically stable engagement between the motor unit and the drive unit, and a coupling mechanism configured to engage with the mechanical connector of the motor unit effective to transfer mechanical power.

21. The system of claim 20 wherein the mechanical power is rotational power.

22. The system of claim 19, wherein the drive unit is configured to engage a shuttle operably connected to a moving member in the housing of the tissue severing unit to operate an operative element on the distal portion of the wand.

23. The system of claim 22, wherein the drive unit includes a drive gear configured to engage a moving member within the housing of the tissue severing unit.

24. The system of claim 23 wherein the moving member is a shaft gear that is effective to rotate the wand of the tissue severing unit.

25. The system of claim 19, wherein the tissue cutting element is a radially deployable cutting element.

26. The system of claim 25 wherein the deployable cutting element is an electrosurgical cutting element.

27. The system of claim 19 wherein the mechanical connector includes a spindle.

* * * * *